United States Patent
Yates

(10) Patent No.: US 10,426,340 B2
(45) Date of Patent: *Oct. 1, 2019

(54) SELF-ILLUMINATED HANDHELD LENS FOR RETINAL EXAMINATION AND PHOTOGRAPHY AND RELATED METHOD THEREOF

(71) Applicant: University of Virginia Patent Foundation, Charlottesville, VA (US)

(72) Inventor: Paul Andrew Yates, Charlottesville, VA (US)

(73) Assignee: University of Virginia Patnet Foundation, Charlottesville, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/794,407

(22) Filed: Oct. 26, 2017

(65) Prior Publication Data

US 2018/0042478 A1    Feb. 15, 2018

Related U.S. Application Data

(60) Continuation of application No. 15/048,279, filed on Feb. 19, 2016, now Pat. No. 9,801,540, which is a continuation-in-part of application No. 14/268,643, filed on May 2, 2014, now Pat. No. 9,265,410, which is a division of application No. 13/318,695, filed as
(Continued)

(51) Int. Cl.
| | |
|---|---|
| *G02C 5/14* | (2006.01) |
| *G02C 5/20* | (2006.01) |
| *A61B 3/15* | (2006.01) |
| *A61B 3/12* | (2006.01) |
| *A61B 3/125* | (2006.01) |
| *A61B 3/00* | (2006.01) |
| *A61B 3/135* | (2006.01) |
| *A61B 3/14* | (2006.01) |
| *G06K 9/00* | (2006.01) |
| *H04N 5/225* | (2006.01) |

(52) U.S. Cl.
CPC ............ *A61B 3/156* (2013.01); *A61B 3/0008* (2013.01); *A61B 3/0025* (2013.01); *A61B 3/12* (2013.01); *A61B 3/125* (2013.01); *A61B 3/1208* (2013.01); *A61B 3/135* (2013.01); *A61B 3/14* (2013.01); *G06K 9/00604* (2013.01); *H04N 5/2251* (2013.01); *H04N 5/2256* (2013.01)

(58) Field of Classification Search
CPC ....... A61B 3/125; A61B 3/117; A61B 3/1015; G02C 7/04; A61F 9/009
USPC ........................................................ 351/219
See application file for complete search history.

(56) References Cited

U.S. PATENT DOCUMENTS

| | | | | |
|---|---|---|---|---|
| 5,200,773 A | * | 4/1993 | Volk | A61B 3/117 351/159.02 |
| 8,550,624 B2 | * | 10/2013 | Padrick | A61B 3/152 351/200 |
| 8,833,934 B1 | * | 9/2014 | Wiser | G02C 7/04 351/159.02 |

* cited by examiner

*Primary Examiner* — Mohammed A Hasan
(74) *Attorney, Agent, or Firm* — Robert J. Decker

(57) ABSTRACT

System and method directed towards providing full and even illumination of a patient's retina through lighting integrated into a handheld fundus lens. By integrating the lighting, the method and system reduces and even eliminate many lens artifacts and reflections. By increasing the accuracy, quality, and field of view 10 afforded during clinical examination of the retina, the method and system will allow practitioners to make more accurate diagnoses and will increase safety during retinal surgical procedures.

6 Claims, 25 Drawing Sheets

Related U.S. Application Data application No. PCT/US2010/033875 on May 6, 2010, now Pat. No. 8,740,383.

(60) Provisional application No. 61/175,807, filed on May 6, 2009.

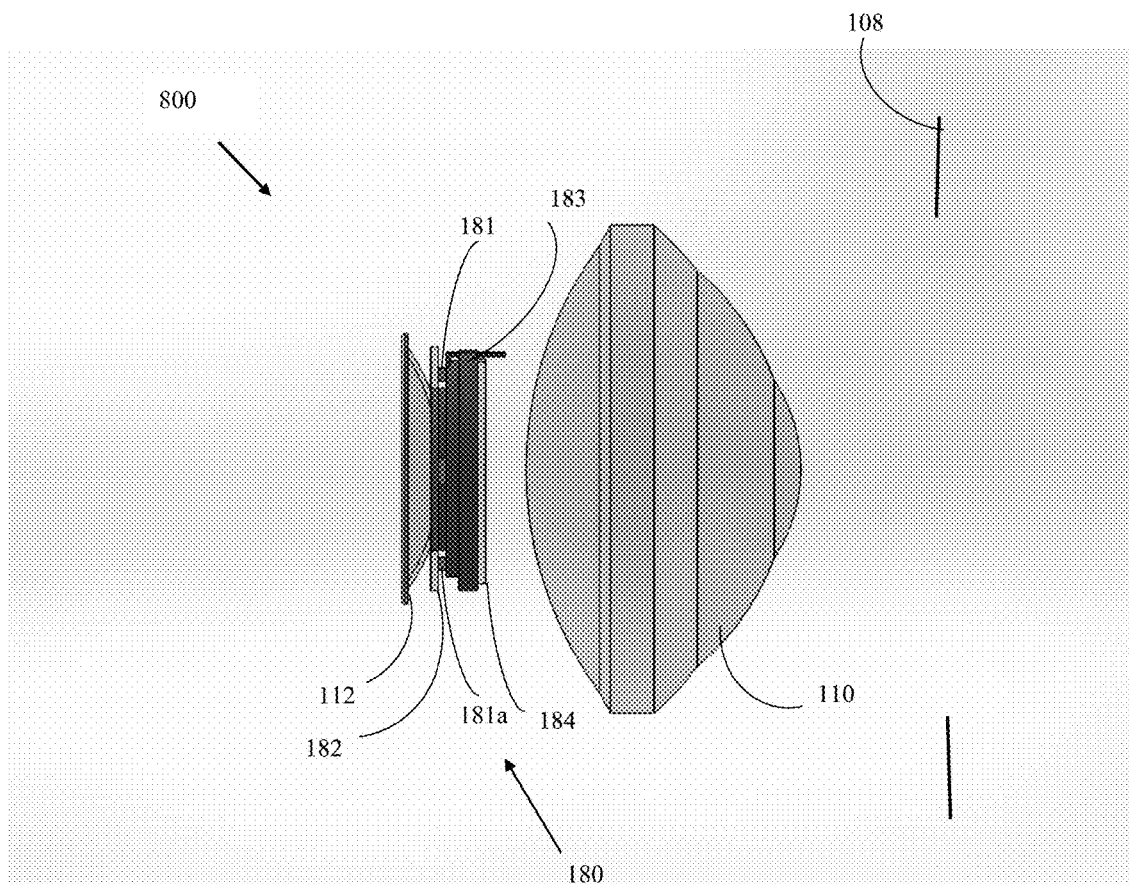
Fig. 17
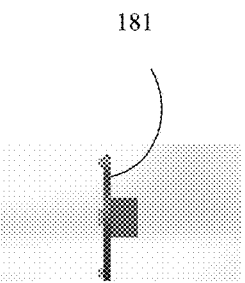 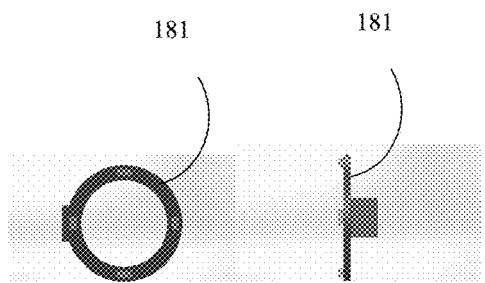
Fig. 18    Fig. 19

SELF-ILLUMINATED HANDHELD LENS FOR RETINAL EXAMINATION AND PHOTOGRAPHY AND RELATED METHOD THEREOF

RELATED APPLICATIONS

This application is a continuation application under 35 U.S.C. § 120 of U.S. patent application Ser. No. 15/048,279, filed Feb. 19, 2016, which is a continuation-in-part (CIP) application of U.S. patent application Ser. No. 14/268,643, filed May 2, 2014, now U.S. Pat. No. 9,265,410, granted on Feb. 23, 2016, which is a division of U.S. patent application Ser. No. 13/318,695, filed Nov. 3, 2011, now U.S. Pat. No. 8,740,383, granted on Jun. 3, 2014, which is a national stage filing of International Application No. PCT/US2010/033875, filed May 6, 2010, which claims the benefit of priority under 35 U.S.C. § 119(e) of U.S. Provisional Application Ser. No. 61/175,807, filed on May 6, 2009, entitled "Self-Illuminated Handheld Lens for Retinal Examination and Photography and Related Method thereof;" the disclosures of which are hereby incorporated by reference herein in their entirety.

FIELD OF THE INVENTION

The present invention is directed to an improved device for retinal examination and related methods. More specifically, aspects of the present invention are directed to handheld fundus lenses with integrated lighting that are self-contained.

BACKGROUND OF THE INVENTION

Clinical examination and treatment of retinal disease has not fundamentally changed in the last 100 years, relying on a slit lamp biomicroscope which consists of a binocular stereo microscope, a handheld condensing lens, and a slit lamp providing illumination to examine the retina, as seen in FIG. 1A. A slit beam of light is created by the slit lamp and shone through a handheld lens placed in front of the patient's eye. The handheld lens produces an image that is visualized through the oculars of the biomicroscope. Unfortunately, this technique suffers from significant image aberrations induced by light reflections off the handheld lens, which limits the practical view to only a thin slice of retina comprising less than 1% of the total retina surface area. FIG. 1B is a typical image of the retina provided by slit beam illumination and a handheld lens. Note the limited field of view and significant lens reflections present. The position of the slit must be maneuvered to examine different parts of the retina. Image quality even from this slit is often significantly degraded, making retinal diagnosis difficult. In contrast, conventional retinal photography routinely is capable of 50 degree aberration and reflection free fields of view of the retina. FIG. 1C is a standard fundus camera image of a retina. There is significantly greater retinal detail and a much wider field of view compared to the slit lamp image of FIG. 1B. No lens reflections or image aberrations are present, greatly facilitating diagnosis of retinal diseases. Unfortunately, these photographic advances have yet to be translated in any meaningful way into improvements in the clinical exam.

There are currently 16 million diabetic patients in the United States who require yearly, dilated retina exams as part of their recommended eye care. Half of these patients will have some form of retinopathy present at the time of exam. For the majority of these patients, slit lamp retinal examination is the only modality used to document their retinal findings. Retina photos are used as an adjunct to the clinical exam in only 10-20% of patients, as this involves separate time consuming procedures by the ophthalmic photographer. This makes it imperative that a clear and reliable view of the retina is available to the clinician for accurate diagnosis.

Ten percent of diabetic patients will eventually develop proliferative diabetic retinopathy, requiring panretinal laser photocoagulation (PRP) to ablate their peripheral retina in an attempt to preserve central foveal vision. FIG. 2A illustrates a retina after PRP. Laser photocoagulation may be delivered via slit lamp techniques using widefield (>75 degree field of view) handheld lenses. These lenses, relying on the same slit illumination, suffer significantly greater reflection artifacts than the narrow field (<75 degree field of view) handheld lenses used for clinical exam of the macula. FIG. 2B illustrates a clinician's view at a slit lamp while performing PRP. A handheld contact lens is applied to a patient's eye and slit lamp illumination is used to visualize the retina and the aiming beam for the laser. Retinal detail is severely compromised from lens reflections and the limited field of view afforded by the slit illumination. The risk of inadvertent laser to the fovea is significant due to the obscuration of the optic nerve by this pattern of poor illumination and lens reflections. The slit beam must be constantly moved to reorient to the location of the optic nerve to verify retinal position and avoid inadvertent ablation of the central vision with laser. The limited and generally poor illumination provided by the slit beam substantially increases the time required for laser treatment and poses a significant and unnecessary safety hazard due to poor identification of retinal location.

Many diabetic patients with proliferative diabetic retinopathy proceed to develop chronic vitreous hemorrhages and decreased vision, requiring surgical removal of the blood in some cases. Poor illumination also poses a safety hazard for their retinal surgery. Standard pars plana vitrectomy technique relies on fiber optic illumination provided by a rigid 20 or 23 gauge probe inserted through the pars plana of the eye. Limited beam divergence of the fiber optic probe provides spot illumination of the retina, with details of the surrounding peripheral retina remaining poorly illuminated, as seen in FIG. 2C. This leads to an increased likelihood of instrument error causing permanent retinal damage. Greater surgical safety and decreased surgical times would be facilitated by a widefield general illumination of the retina in addition to the spot illumination provided by the fiber optic probe.

Commercial developments in ophthalmic photography over the last 40 years have clearly demonstrated that the retina can be imaged at high resolution and that image distortions/reflections can be fully corrected to enable accurate diagnosis of retinal disease. The hallmark of the difference in retinal photography over clinical exams is the different pattern of illumination used in each, as illustrated in FIG. 3A. Contemporary retina cameras generate a ring or "donut" of illumination centered on the pupil. This circular illumination provides an even/full illumination of the retina with minimal lens reflections. Imaging rays reflected from the back of the retina are collected from the middle of the "donut," which substantially decreases lens reflections. Most commercial retina cameras are able to obtain a 50 degree field of view of the retina with this technique FIG. 1C, but are not able to achieve widefield (>75 degrees field of view) images such as shown in FIG. 2A.

Narrowfield cameras are non-contact, with the camera never touching the front surface of the eye. In contrast, widefield cameras often require direct contact of the imaging system with the cornea. The commercial RETCAM II retinal camera is an example of a widefield camera which directly contacts the cornea. This camera creates a donut of light using a solid fiber optic ring to couple an external illumination light directly to the cornea, as shown in FIG. 3E. FIG. 3C shows a sample image from the Retcam II. This illumination design, while a significant improvement on slit lamp illumination, still suffers from significant corneal haze, as well as unevenness in central illumination, as compared to peripheral illumination, due to issues with the illumination design. Further, the RETCAM II is designed for retinal photography and as specified is not capable of use in handheld clinical examination through a slit lamp biomicroscope. The device has electrical power and fiber optic light coupled into a sizable imaging wand that is significantly larger than existing handheld fundus lenses, severely limiting the unit's portability and ease of use. The design of the illuminating ring requires intricate manufacturing that would not be amenable to inexpensive handheld lenses. All these issues are addressed in various embodiments of the present invention, which is a significant improvement over contemporary designs.

An improved method of illumination is needed to provide a wider field of view of the retina and to eliminate those lens reflections that result from external slit illumination of the handheld condensing lens. The ideal illumination for the retina is a ring of light focused on the eye with a diameter slightly less than the pupil diameter. Prior designs (Pomerantzeff et al., U.S. Pat. No. 3,944,341, and Massie et al., U.S. Pat. No. 5,822,036, of which are incorporated by reference herein in their entirety) have adapted a method of illumination into designs for retinal photography, as opposed to clinical examination. These two designs rely on an external illumination device that is then routed by means of fiber optic coupling into a contact lens that is used to view the retina.

These existing devices, while may be an improvement over non-illuminated handheld lenses, suffer from a number of design constraints that do not allow them to be used for handheld fundus examination at the ophthalmic slit lamp. Pomerantzeff relies on two rows of individual fiber optic elements that are cemented into a contact lens with the fiber optics directly contacting the cornea. This presents issues with sterilization due to the inevitable breakdown of the cementing compound and lodging of bacteria into the cemented area surrounding it. It also requires technically difficult fiber optic polishing so that the individual fibers do not damage the cornea and are all at the same plane. By focusing the ring of light on the cornea through means of fiber optics, significant corneal haze is generated which lowers overall image contrast. There is a complicated five stage optical element design to produce an image which leads to an unnecessarily bulky lens that could not be easily manufactured or handheld due to its overall size. The directionality of the fiber optics, while illuminating some of the peripheral retina, do not illuminate the central portion of the retina well, leaving the macula less exposed to light compared to the peripheral retina. A separate illuminator is required that is external to the device, requires electrical power, and limits portability of this device. The device is intended for retinal photography and is not optimized or usable for slit lamp examination. The focus of the five lens design is intended to focus reflected retina light on an imaging device directly attached to the lens, rather than at the distances required by ophthalmic slit lamp examination. Finally, the patent has not resulted in a commercial device in the 30 years since it was originally issued.

The patent by Massie et al. has similar limitations to the earlier design of Pomerantzeff. Fiber optic illumination is used to direct the light from an external illumination source into the imaging lens, reducing portability of the unit. The device is intended only for retinal photography with an imaging device built into the handheld unit and then electrically connected to a larger external imaging control unit. There is no clear optical axis that would allow use of the device at the ophthalmic slit lamp. The design is intended to focus the light from the retina onto an imaging device that is located directly behind the contact lens rather than at the distances required by handheld condensing lenses used at an ophthalmic slit lamp. The use of fiber optics for coupling of an external illumination source limits the diffusion of the illuminating light beam and provides only partial illumination of the retina with a dark central retina, as also seen with the Pomerantzeff design. While the Massie design allows for illumination by placing a second central illumination source contained within the handheld unit itself to illuminate central retina, it obscures the central axis of the lens, which eliminates visualization of the retina through the center of the lens; a function essential to a handheld condensing lens. The design additionally attempts to improve the illumination produced by fiber optic through use of up to three additional lens elements at the end of the fiber optic, which again complicates construction and alignment of this device. Similar to the Pomerantzeff design, Massie's coupling of light fiber optically directly to the corneal surface results in significant corneal haze which degrades image contrast.

Fine polishing of the fiber optic is required to angle the exit of the light to improve the area of the retina illuminated. However, the angle cut required on the fiber optic reduces transmission of the light due to the oblique exit of the light from the fiber optic element. Finally, the design of the Massie device results in a bulky imaging unit that far exceeds the typical 40 mm depth of a handheld fundus lens. All of these design issues that are optimized for retinal photography limit the ability of this design to be used as a self illuminated handheld condensing lens for retinal examination.

Next, Miller et al., U.S. Pat. No. 7,048,379, discloses an imaging lens and illumination system for a retinal camera. Miller's ring illumination was focused on the patient's retina through a front objective lens. The lighting is located behind the objective lens, and the camera is not designed with a contact lens.

Contemporary retinal photography designs are capable of attaining better quality images and a wider field of view with less reflections than conventional slit lamp illumination. However, they remain limited by size, portability, poor illumination, and poor image contrast. Massie and Pomerantzeff produced devices which have no direct view through the lens that is available for the practitioner to directly visualize the retina (as both are intended for retinal photography) and are too large to be of practical use in clinical examination. Further, their complicated designs render them expensive to manufacture. Finally, they still suffer from problems with full and even illumination.

Providing the versatility and speed of clinical examination with the accuracy and clarity of retinal photography would provide greatly improved image quality, permitting significantly wider fields of view, better resolution of retinal detail for diagnosis, and safer surgical intervention to treat retinal disease.

SUMMARY OF THE INVENTION

An aspect of an embodiment of the present invention seeks to correct the illumination issues with current handheld fundus lenses. The slit lamp biomicroscope may be used to view the image through the handheld retina lens, but the handheld lens itself would provide the illumination of the retina, rather than relying on slit illumination provided by the slit lamp. An aspect of various embodiments of the present invention captures the illumination characteristics of retinal camera design in miniature, creating a design that may be battery powered and simple to manufacture, maintaining commercial viability. An embodiment provides, among other things, a handheld lens where ring illumination is directly coupled to the contact lens portion of the handheld lens, as illustrated in FIG. 3B. This creates a ring or "donut" of illumination that is transmitted to the eye when the front contact lens of the device is applied to the cornea. This ring could be created through many designs, including a ring of surface mount LEDs, the use of fiber optics to fashion donut illumination from a point source of light, the use of a shaped mirror to provide a dispersed donut of light, and a curved surface with surface mount LEDs providing multidirectional illumination. FIG. 3D illustrates the potential viewing area of such a widefield handheld contact imaging lens of FIG. 3B.

An aspect of an embodiment of the present invention provides a self-illuminated handheld lens (and related method) to aid in the examination and treatment of retinal disease. Retinal exams and retinal laser treatments are commonly performed using a slit lamp biomicroscope. The slit lamp uses a narrow beam of light that illuminates less than 1% of the total retinal surface and suffers from significant optical aberrations that obscure retinal details. To alleviate these problems, an embodiment of the present invention provides a self-illuminated handheld fundus lens for retinal imaging to be used in conjunction with the slit lamp biomicroscope to provide clear, reflection free, wide field illumination and view of the retina. An aspect of an embodiment of the present invention device creates ring illumination that is coupled through the contact lens of a handheld fundus lens to provide this widefield illumination of the retina. An embodiment of the present invention device may rely on use of fiber optics and/or light emitting diodes to provide illumination, though many other means of illumination are possible.

An aspect of an embodiment of the present invention provides a self-illuminated handheld device for retinal examination of a subject. The device may comprise: a viewing lens; a contact lens to be applied to an eye; an integrated light source; an annular light channel through which light from the integrated light source is transmitted to the eye; and a light baffle separating the integrated light source and the light channel from a central aperture between the viewing lens and the contact lens.

An aspect of an embodiment of the present invention provides a system and related method for retinal photography. The system includes a self-illuminated handheld fundus lens, whereby the self-illuminated fundus lens may comprise: a viewing lens; a contact lens to be applied to an eye of a subject; an integrated light source; an annular light channel through which light from the integrated light source is transmitted to the eye; and a light baffle separating the integrated light source and the light channel from a central aperture between the viewing lens and the contact lens. Moreover, the system may also include: an image recording device; and a lens-to-camera interface, adapted to transmit an image from the lens to the image recording device.

An aspect of an embodiment of the present invention provides a self-illuminated handheld device (and related method) for retinal examination of a subject. The device may comprise: a viewing lens; a contact lens to be applied to an eye; an integrated light source; an annular light channel through which light from the integrated light source is transmitted to the eye, the annular light channel is a thinning of the contact lens, a portion of the contact lens that differs in power, a gap ground into or provided in the contact lens, a gap around or adjacent to the contact lens, or a space behind or adjacent to the contact lens and is located behind, around, adjacent to or through the contact lens; a light baffle separating the integrated light source and the light channel from a central aperture between the viewing lens and the contact lens; and an integrated power source in communication with the integrated light source.

An aspect of an embodiment provides a self-illuminated handheld lens for wide angle retinal viewing of a subject eye, comprising: an aspherical objective lens having a symmetric viewing axis and defining a viewing channel; plurality of LEDs positioned around the viewing axis and configured to emit light to illuminate the subject eye; an electronic controller powering the plurality of LEDs and controlling each individual LED or a series of LEDs independently; a light baffle configured to block stray light of the plurality of LEDs from getting into the viewing channel; and a cross polarization means incorporated between the plurality of LEDs and the viewing channel of the aspherical objective lens, wherein the cross polarization means comprises a first polarizer to polarize the light emitted from the plurality of LEDs and a second polarizer positioned in the viewing channel of the aspherical objective lens. An aspect of an embodiment of the present invention provides a method (and related system) for illuminating the cornea/retina of an eye of a subject through a handheld device. The method may comprise: generating light from one or more light sources; reflecting the light off a mirrored surface; transmitting the light through an annular light channel proximal to a contact lens; and receiving an illuminated image from the eye through a viewing lens.

These and other objects, along with advantages and features of various aspects of embodiments of the invention disclosed herein, will be made more apparent from the description, drawings and claims that follow.

BRIEF DESCRIPTION OF THE DRAWINGS

The accompanying drawings, which are incorporated into and form a part of the instant specification, illustrate several aspects and embodiments of the present invention and, together with the description herein, serve to explain the principles of the invention. The drawings are provided only for the purpose of illustrating select embodiments of the invention and are not to be construed as limiting the invention.

FIG. 17 shows a CAD drawing of self-illuminated wide angle contact lens implemented a front LED illumination module with cross polarization.

FIG. 18 shows a front view of FIG. 17 of a LED circular array for front LED illumination.

FIG. 19 shows a side view of FIG. 17 of a LED circular array for front LED illumination.

DETAILED DESCRIPTION OF THE INVENTION

Aspects of the present invention are directed towards providing full and even illumination of a patient's retina through lighting integrated into a handheld fundus lens. By integrating the lighting, aspects of the present invention reduce and even eliminate many lens artifacts and reflections. By increasing the accuracy, quality, and field of view afforded during clinical examination of the retina, an aspect of the present invention will allow practitioners to make more accurate diagnoses and will increase safety during retinal surgical procedures.

An aspect of an embodiment of the current invention is designed to provide, among other things, self-contained ring illumination of the retina within the space constraints of a handheld fundus lens which measures approximately 40 mm×50 mm×20 mm, and optimized for visualization of retinal details by a trained practitioner at an ophthalmic slit lamp. As portability of the unit may be advantageous to marketability and acceptance of this device, the design may be focused on this design constraint for the various embodiments of this invention. While this specific size is the average size of a handheld lens, it will be readily understood that larger lenses may still meet the handheld design constraint. We also consider other embodiments that meet some but not all of these design constraints, as they may be preferred under certain circumstances. It should be appreciated that the devices and systems of the various embodiments discussed throughout this disclosure may be implemented to be larger or smaller than the dimensions of 40 mm×50 mm×20 mm, as desired or required.

Several embodiments of the present invention are discussed below. However, the invention may be embodied in other forms without departing from the spirit or essential characteristics of the present invention. It is therefore to be understood that the following embodiments are to be considered illustrative rather than limiting of the invention described herein.

Figure 1A:
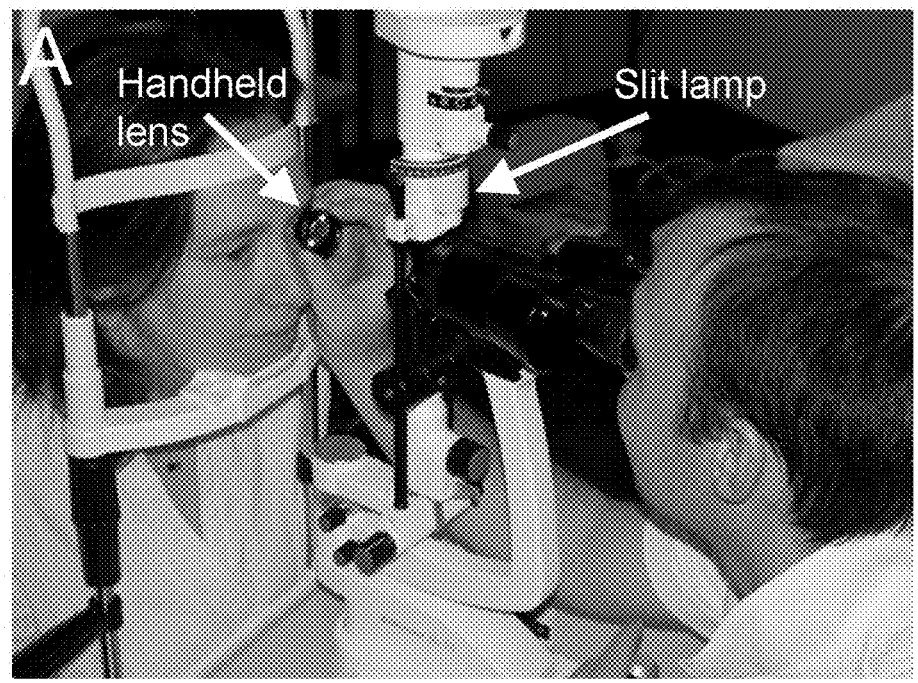
FIG. 1A illustrates a slit lamp biomicroscope.
Figure 1B:
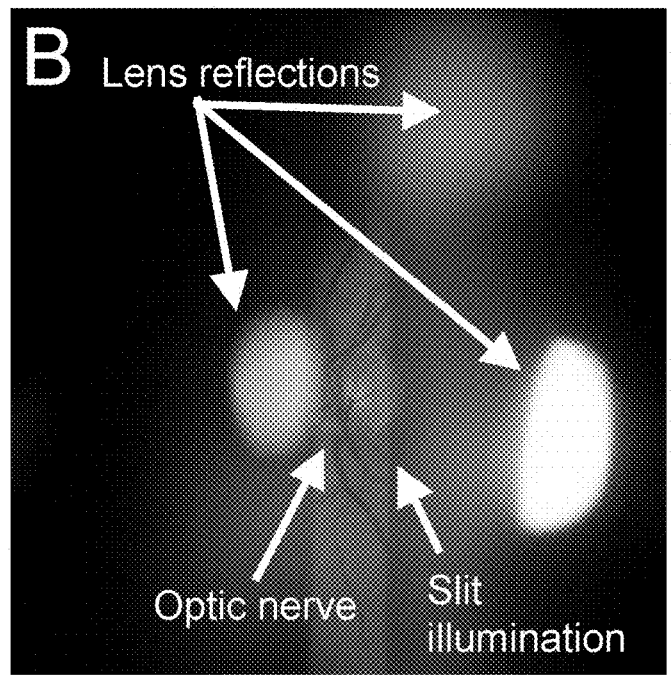
FIG. 1B demonstrates a typical image provided by a slit lamp biomicroscope with use of a contemporary handheld lens and standard slit lamp illumination.
Figure 1C:
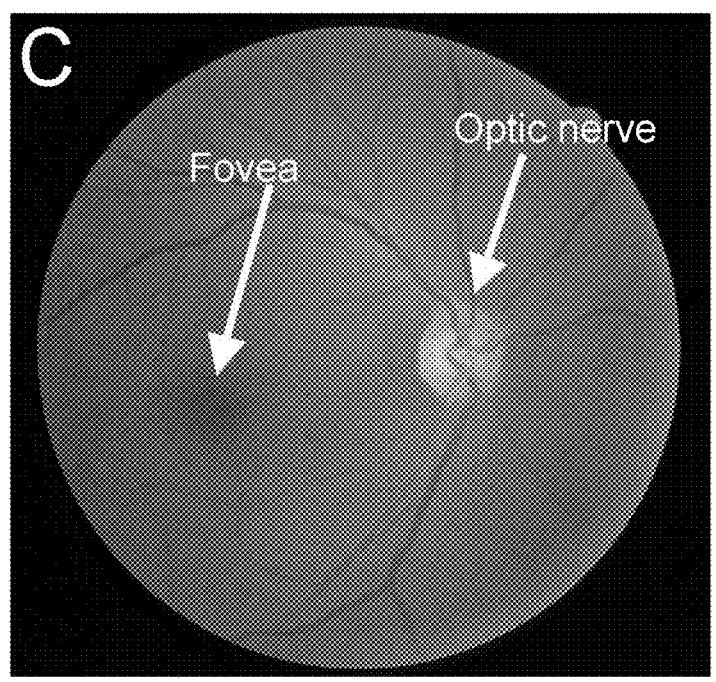
FIG. 1C demonstrates a typical image provided by a fundus camera, with the same scale as used in FIG. 1B.
Figure 2A:
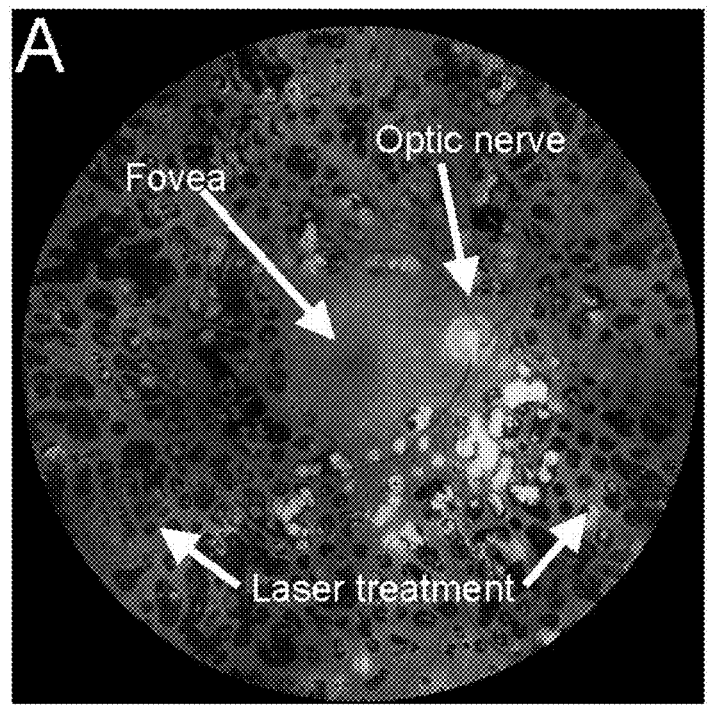
FIG. 2A illustrates a retina after undergoing panretinal photocoagulation (PRP) for treatment of proliferative diabetic retinopathy.
Figure 2B:
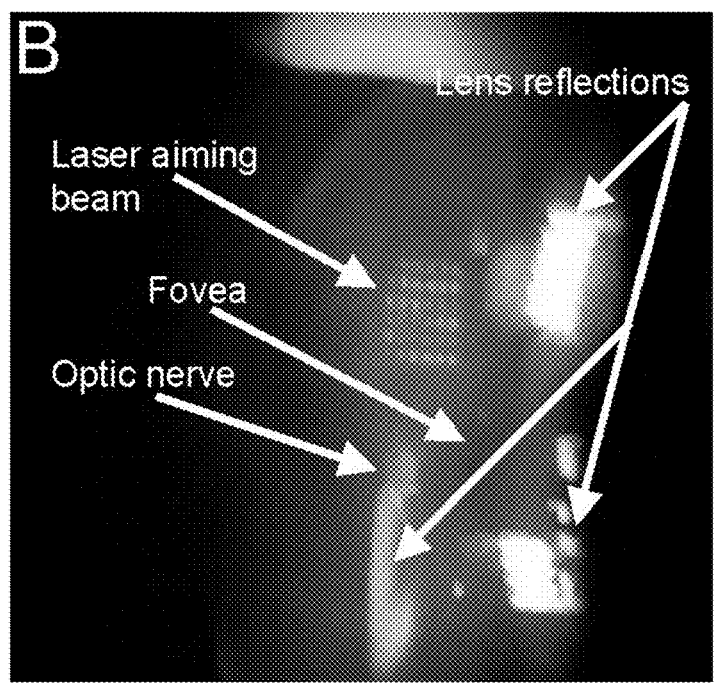
FIG. 2B illustrates a clinician's view at a slit lamp biomicroscope during performance of PRP using a contemporary widefield handheld lens with standard slit lamp illumination.
Figure 2C:
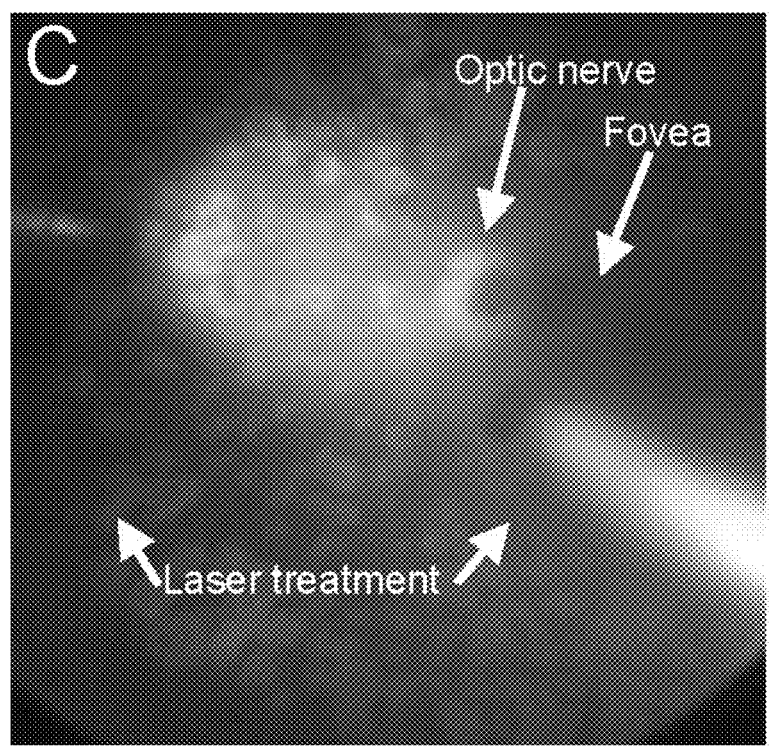
FIG. 2C illustrates a retina surgeons's view through an operating microscope during pars plana vitrectomy surgery.
Figure 3A:
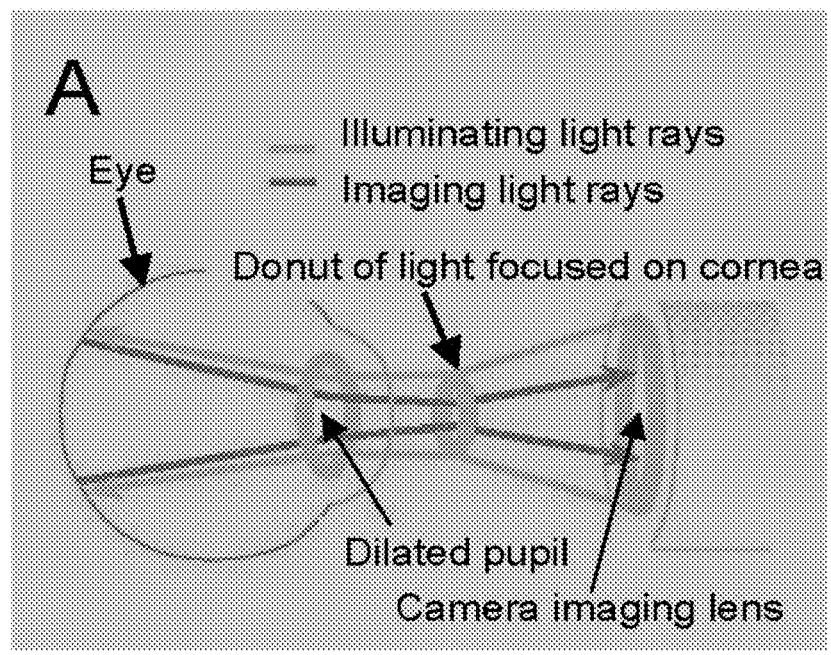
FIG. 3A illustrates the typical "donut" illumination used by most commercial retina cameras.
Figure 3C:
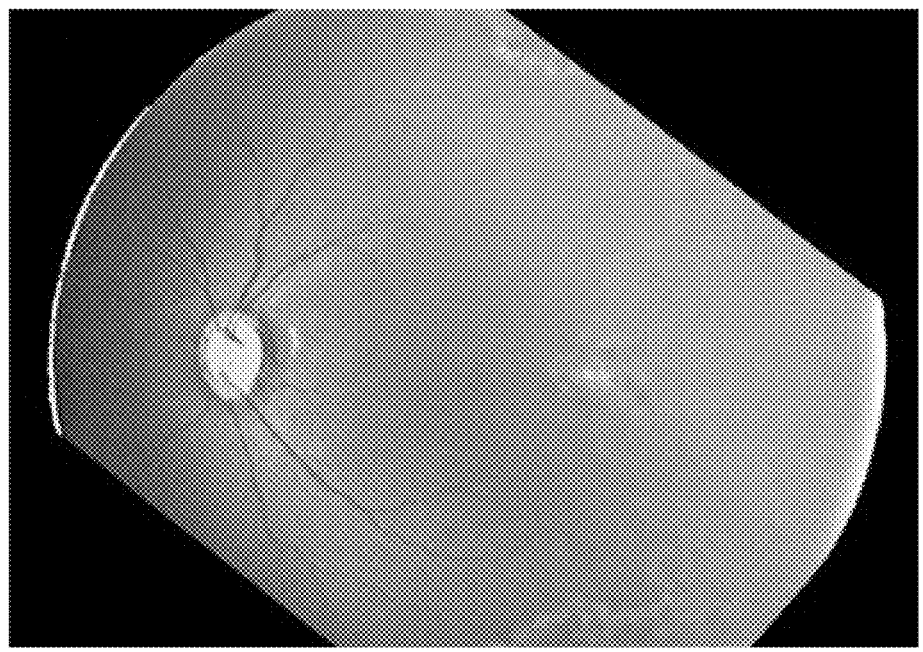
FIG. 3C demonstrates a sample image and design of a commercial retina camera.
Figure 3B:
FIG. 3B illustrates an embodiment of the present invention handheld fundus lens that provides its own ring illumination built into its contact lens.
Figure 3D:
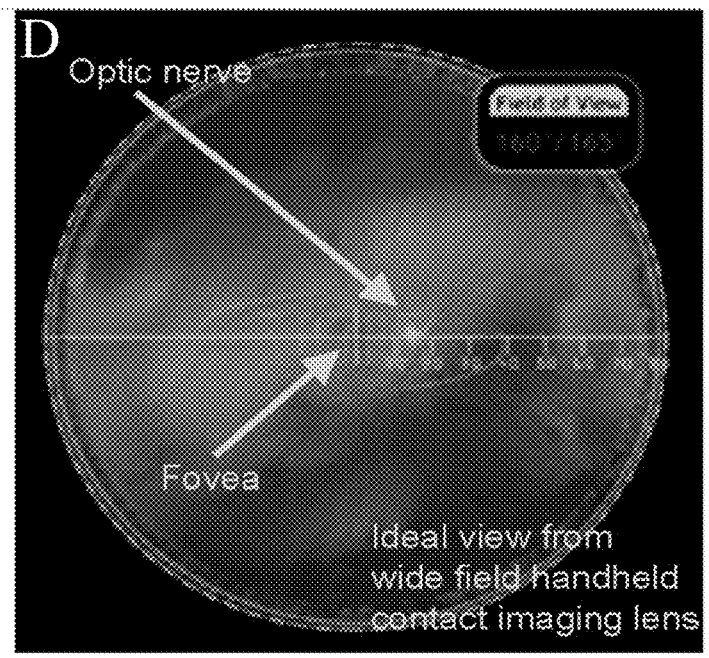
FIG. 3D illustrates the field of view obtained by the widefield lens of FIG. 3B, which can visualize the full 165 degrees field of view of the retina.
Figure 3E:
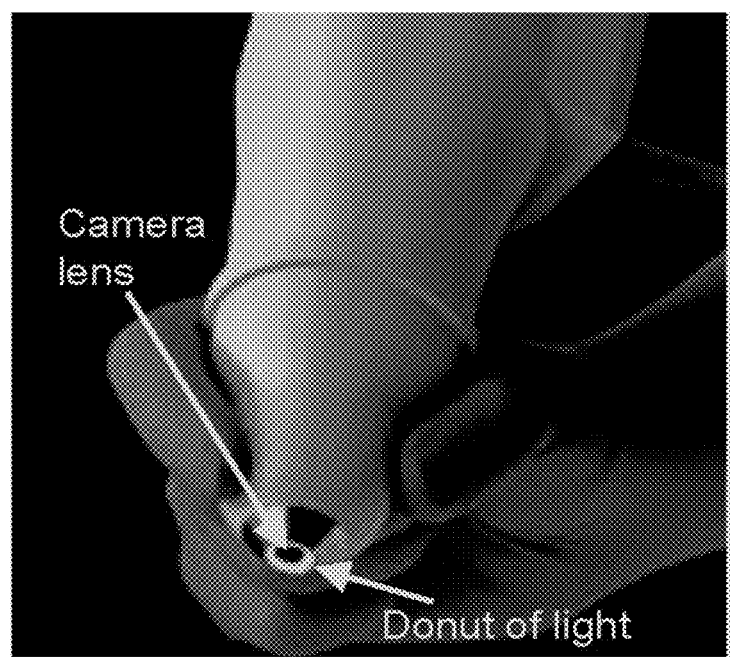
FIG. 3E shows the commercial retinal camera, RETCAM II.
Figure 4:
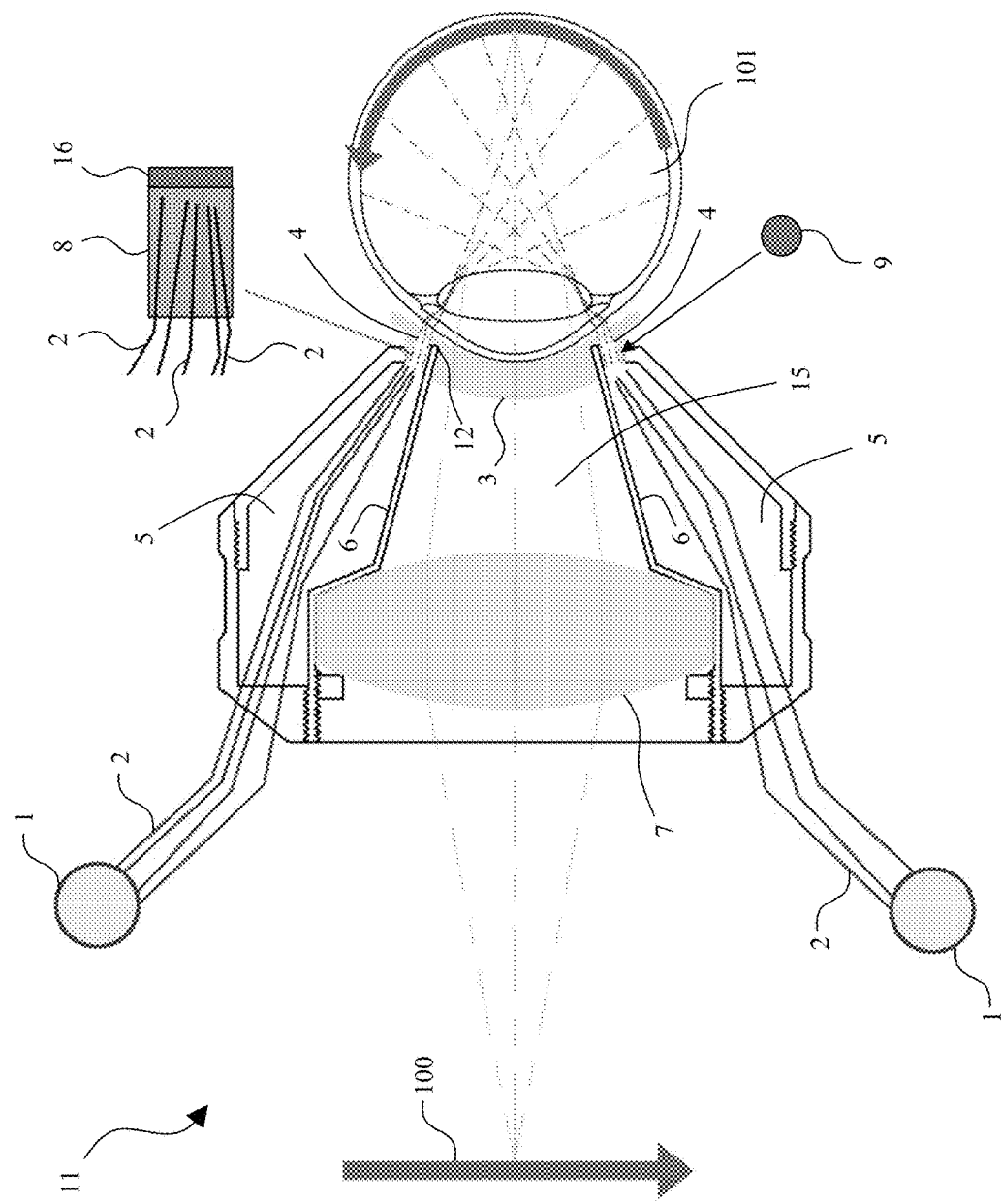
FIG. 4 schematically illustrates an embodiment of the present invention, utilizing fiber optic cables to couple light from either an external light source, or a light source built into the handheld lens itself to illuminate the retina.

An embodiment of the present invention provides a handheld lens 11 for illuminating a patient's retina 101 from a point source of light through fiber optics cables. This embodiment is illustrated in FIG. 4. In this embodiment, there is a light source 1 outside of the lens that is directly coupled to fiber optic cable 2. Light source 1 may be any bright light. In one embodiment it would consist of a white, infrared, or color high intensity LED light source as these light sources have low power requirements amenable to battery power. In another embodiment it would include halogen or xenon flash lighting which may or may not require electrical line power to achieve higher intensity illumination than could be provided by LEDs. The fiber optic cable 2 may be composed of multiple thin fiberoptic strands. These individual strands are reformed into a ring illumination that directly abuts the contact lens 3. A light channel 4 is ground into the contact lens 3 and fiber optic cable 2 inserts into this light channel 4. The light channel 4 may be around, through, adjacent or behind contact lens 3. It is through the light channel 4 that light from the fiber optic cable 2 is transmitted to the retina 101. The light channel 4 may be a thinning of the contact lens 3, a portion of the contact lens 3 that differs in power, a gap ground into or provided in the contact lens 3, a gap around or adjacent to the contact lens 3, or a space behind or adjacent to the contact lens 3. The fiber optic cable 2 is located in a separate light cavity 5 of the handheld lens 11 with a light baffle 6 to prevent stray light from entering the central aperture 12 of the lens cavity 15 and the viewing field of a viewing lens 7. The sides of the light channel 4 are covered with material to prevent transmission of stray light from the light channel 4 into contact lens 3 which would obscure the image viewed through the viewing lens 7. Light from the light source 1, transmitted through the fiber optic cable 2 and light channel 4 to the retina 101, reflects back through the contact lens 3 and viewing lens 7 resulting in an image 100.

Contemporary designs utilized an angle cut and polished solid one-piece fiber optic insert to transmit light to the contact lens. As has been noted, this has the disadvantage of decreasing transmission of light from the end of the fiberoptic due to the oblique angle of the cut end. Further, light emerging from the end of the fiberoptic does not provide a diffuse light source as is required to illuminate the entire retina. One aspect of the current invention solves this limitation through a diffusing insert. Two exemplary implementations are now described. In the first, the individual fiber optic strands of fiber optic cable 2 enter a fiber optic block 8 perpendicular to its surface. The fiber optic block 8 is optionally inserted into the light channel 4. Each strand of the fiber optic cable 2 is threaded into a hole in the fiber optic block 8. The hole for each strand of the fiber optic cable 2 is progressively angled so that the directionality of light from the individual strands as they emerge at the distal end of the fiber optic block 8 is different. This allows illumination to be directed from individual fibers both centrally and peripherally so that no difference in illumination occurs as was found in contemporary designs. A second exemplary approach is to optionally embed a mini-optical diffuser 9 within the light channel 4, replacing the fiber optic block 8. A Mini-optical diffuser 9 scatters the incident light from the incoming strands of the fiber optic cable 2, thereby reducing the strong directionality of the fiberoptic light. This provides more even illumination with multidirectionality of light to provide even illumination of both peripheral and central retina than contemporary designs. This is also a technically more efficient and pragmatic design than the multiple added lens elements used in contemporary designs to reduce the directionality of the light.

In order to obtain selective illumination of the retina 101, an adjustable optical mask 16 may be used. This mask may be physical, such as an adjustable diaphragm, or electronic, such as a transparent liquid crystal display. Use of the adjustable optical mask 16 would allow a clinician to control which portion of the retina 101 is illuminated.

Figure 5:
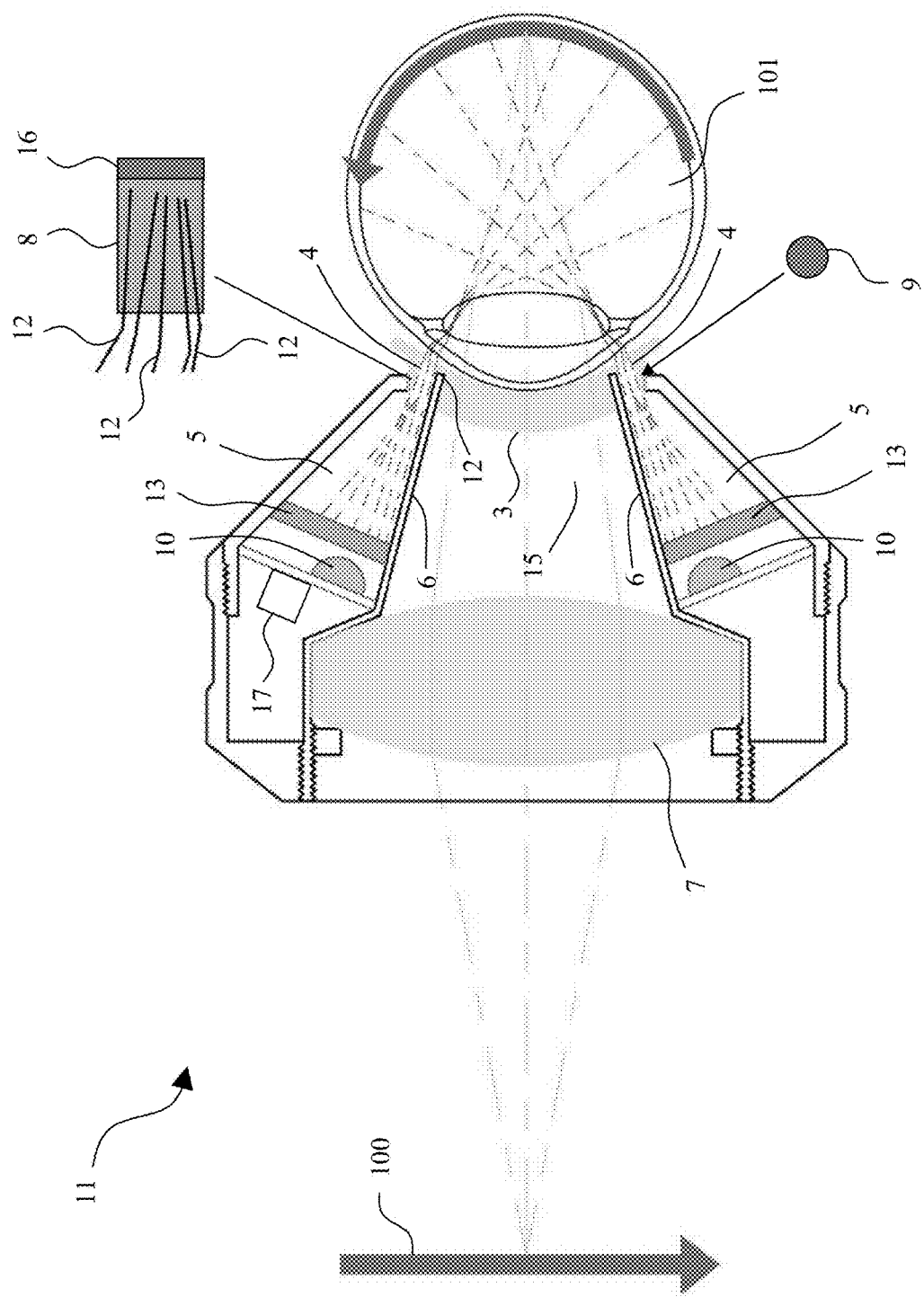
FIG. 5 schematically illustrates an embodiment of the present invention, utilizing light emitting diodes to illuminate the retina.

Another embodiment of the present invention provides a handheld lens 11 utilizing a ring of light-emitting diodes (LEDs) to provide illumination to the retina 101 and is illustrated in FIG. 5. The illustrated embodiment provides ring illumination directly within handheld lens 11 using a ring of LEDs 10. LEDs 10 may be high intensity white, infrared, or colored. Utilizing different types of LEDs allows for imaging of either red free, infrared, or fluorescent dyes which are commonly used to evaluate retinal function. In one implementation of this embodiment, an optical diffuser 13 is used to reduce the point source characteristics of the LEDs 10. The light from the LEDs 10 remains contained within the light cavity 5 and light baffle 6 so that stray light does not enter the central aperture 12 of the lens cavity 15 or the viewing area of the viewing lens 7. The light enters the light channel 4 and is transmitted to the retina 101. As the sides of light channel 4 are coated to block light from entering contact lens 3, an effective optical circular ring mask is created. Light is only transmitted from the distal end of the light channel 4, directly adjacent to the patient's cornea. It is through the light channel 4 that light from LEDs 10 is transmitted to the retina 101. The light channel 4 may be a thinning of the contact lens 3, a portion of the contact lens 3 that differs in power, a gap ground into or provided in the contact lens 3, a gap around or adjacent to the contact lens 3, or a space behind or adjacent to the contact lens 3. Light from the LEDs 10, transmitted through the light channel 4 to the retina 101, reflects back through the contact lens 3 and viewing lens 7 resulting in an image 100.

In cases where central or mid peripheral retinal illumination is required, this will provide sufficient even illumination of the retina. In instances where a wider field of illumination is needed, a mini-optical diffuser 9 at the distal end of the light channel 4 is used to scatter the illumination evenly across the entire retina. An alternative embodiment is to place a fiber optic ring block 8 into the light channel 4. Small lengths of fiber optic strands 12 run throughout the fiber optic block 8. As in the preceding embodiment, the small lengths of fiber optic strands 12 may be angled to redirect the light at all incident angles to provide full and even illumination of central and peripheral retina.

In some contemporary designs, two rings of fiberoptic illumination were embedded into the contact lens to adjust for different pupil sizes. Either one or the other ring would be illuminated to provide the optimal retinal illumination. One aspect of the present invention proposes to address this by placing an adjustable optical mask 16 within light channel 4. The size of the adjustable optical mask 16, limiting the amount and shape of the light passing through the contact lens 3, may be controlled by the practitioner according to required pupil size. This may be done either mechanically through manual adjustment of an embedded diaphragm or in an alternative embodiment an electronic transparent LCD is embedded into the light channel 4 and individual pixels are controlled electronically to set the size of the ring mask. Thus, the device can be used on multiple patients and the size of the ring illumination customized to their particular pupil size to provide optimal retinal illumination.

In order to obtain selective illumination of the retina 101 by the LEDs 10, a controller 17, such as a microcontroller, may be used. This controller 17 allows for control of which LEDs of LEDs 10 are illuminated, for how long (e.g., various temporal characteristics), and how bright. Use of controller 17 would allow a clinician to control which portion of the retina 101 is illuminated (e.g., pattern or spatial arrangement).

It should be appreciated that a controller and/or processor may be in communication with any of the components or systems disclosed herein, as desired or required.

Figure 6:
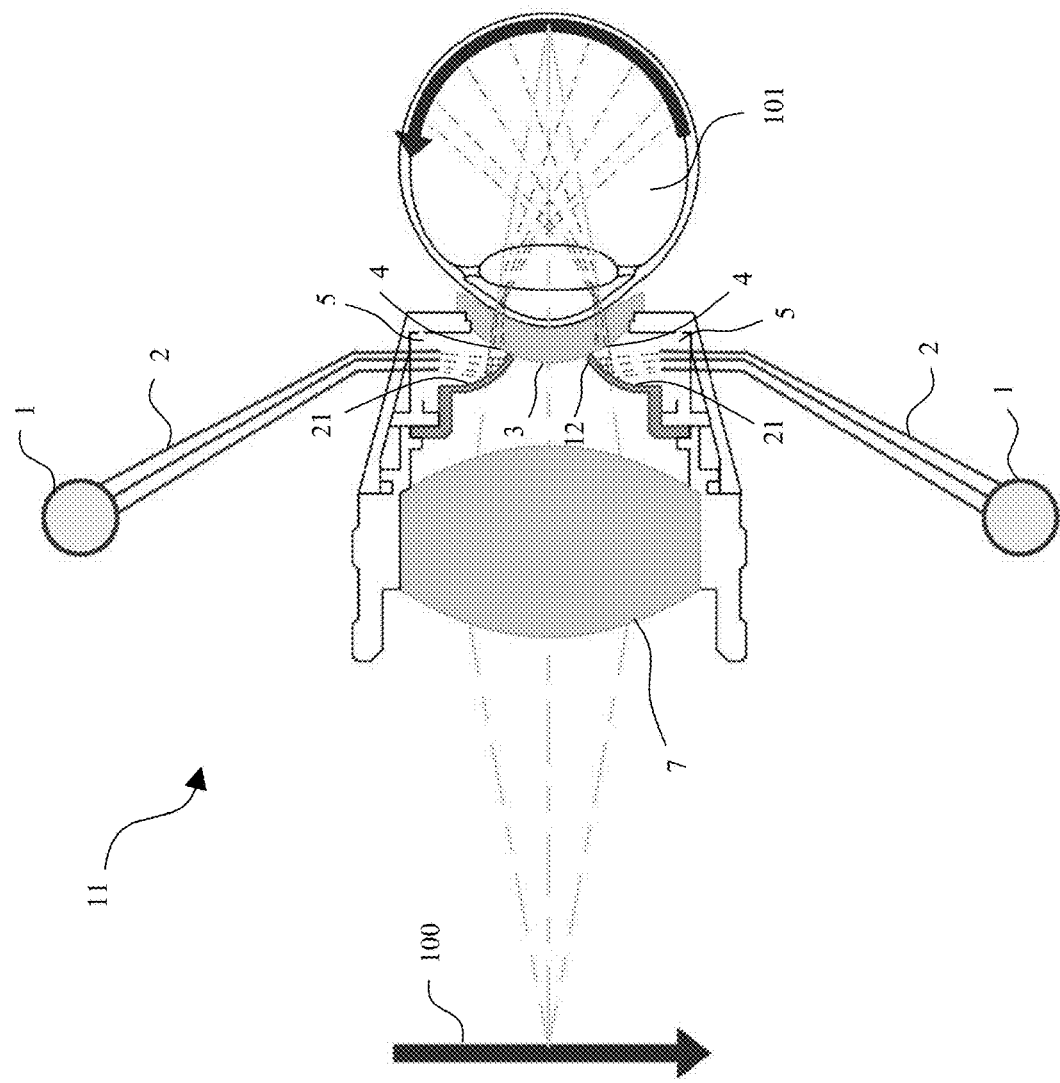
FIG. 6 schematically illustrates an embodiment of the present invention, utilizing a combination of fiber optic cables and a mirrored surface to illuminate the retina.

Another embodiment of the present invention provides a handheld lens 11, which involves the use of an annular mirror to scatter light from a light source and transmit it to a patient's eye. One such embodiment is illustrated in FIG. 6. In this embodiment, the shape of the mirror is designed to create even illumination of both central and peripheral retina. The fiber optic cable 2 is used to transmit light from the light source 1 through the light cavity 5. The light source 1 may be any bright light. In an embodiment it may consist of a white, infrared, or color high intensity LED light source as these light sources have low power requirements amenable to battery power. In another embodiment it would include halogen or xenon flash lighting, which may or may not require electrical line power to achieve higher intensity illumination than could be provided by LEDs. The fiber optic cable 2 may be composed of multiple thin fiberoptic strands. The light from the fiber optic cable 2 is then reflected off of the mirrored surface 21 through the light channel 4 and contact lens 3, into the patient's eye. It is through the light channel 4 that light from the LEDs 10 is transmitted to the retina 101. The light channel 4 may be a thinning of the contact lens 3, a portion of contact lens 3 that differs in power, a gap ground into or provided in the contact lens 3, a gap around or adjacent the contact lens 3, or a space behind or adjacent to the contact lens 3. In one embodiment, the mirrored surface 21 is designed to provide even illumination of the retina by reducing the directionality of the light. The mirrored surface 21 also prevents light from entering the central aperture 12 of the lens cavity 15 and the viewing area of the viewing lens 7. In this sense, the mirrored surface 21 serves a similar purpose to the light baffle 6. The focus point for the scattered light reflected from the mirrored surface is not at the corneal surface as occurs with contemporary fiber optic designs. This feature significantly reduces corneal haze that is present in contemporary designs. Light from the light source 1, transmitted through the fiber optic cable 2, off of the mirrored surface 21, and through the light channel 4 to the retina 101, reflects back through the contact lens 3 and the viewing lens 7 resulting in an image 100.

Figure 7:
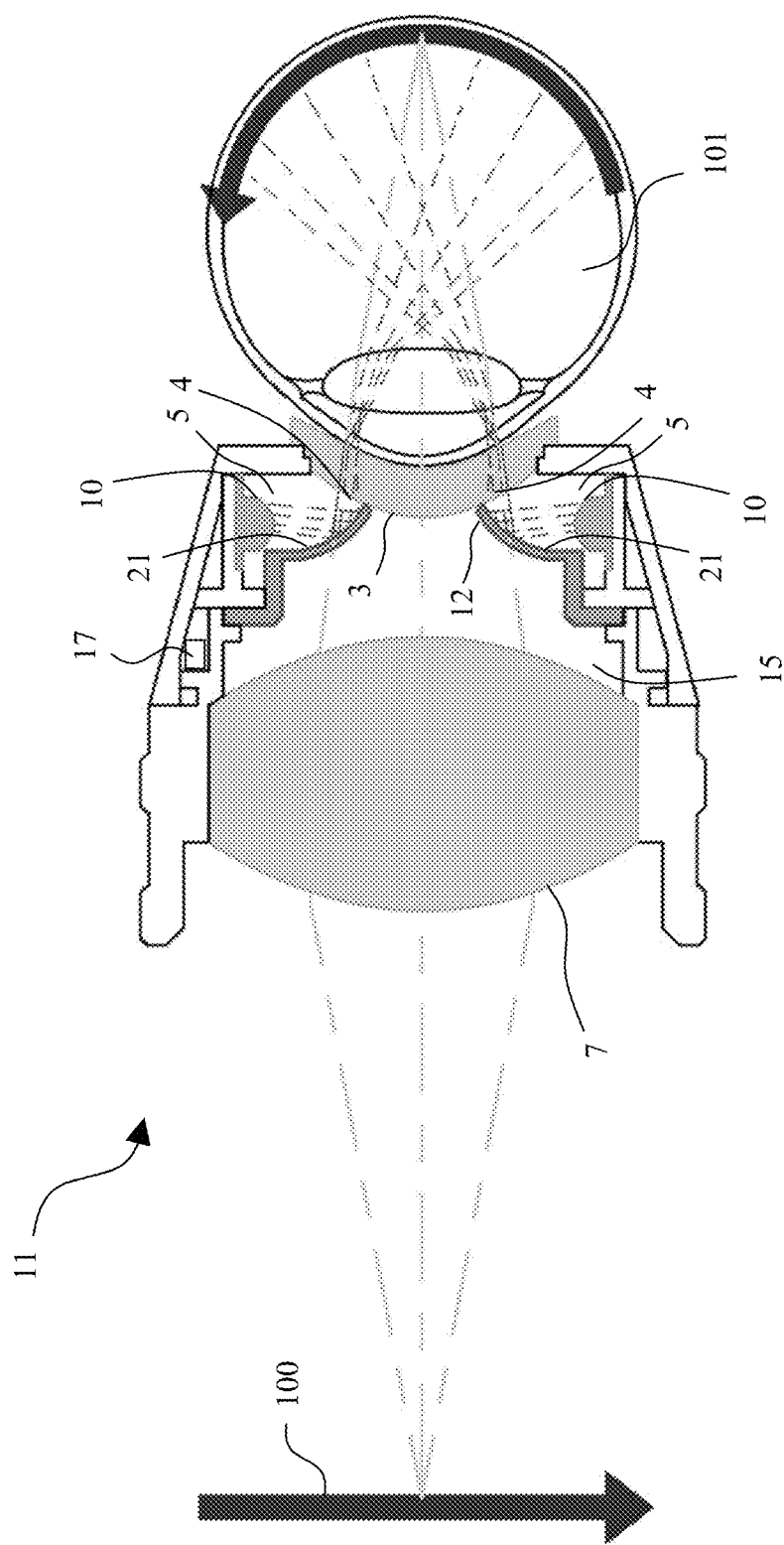
FIG. 7 schematically illustrates an embodiment of the present invention, utilizing a combination of light emitting diodes and a mirrored surface to illuminate the retina.

A similar embodiment is illustrated in FIG. 7. This embodiment provides a handheld lens 11 which utilizes a ring of the surface mounted LEDs 10 and a mirrored surface 21 to illuminate a patient's retina 101, providing a ring of light. Light from the LEDs 10 is emitted in the light cavity 5. The LEDs 10 may be high-intensity white, infrared, or colored. The light is reflected off of the mirrored surface 21 through the light channel 4 and contact lens 3, into the patient's eye. In an embodiment, the mirrored surface 21 is designed to provide even illumination of the retina by reducing the directionality of the light. In other embodiments, the mirrored surface can be shaped to provide a different pattern of retinal illumination needed for a particular use. The mirrored surface 21 also prevents light from entering the central aperture 12 of the lens cavity 15 and the viewing area of the viewing lens 7. In this sense, mirrored surface 21 serves a purpose similar to the light baffle 6. Light from the LEDs 10, transmitted off of the mirrored surface 21 and through light channel 4 to the retina 101, reflects back through the contact lens 3 and viewing lens 7 resulting in an image 100.

An embodiment of the present invention allows a practitioner control over the illumination pattern by direct control of individual LEDs 10. A controller 17 is connected to each individual LED or a series of LEDs to allow a practitioner spatial, temporal, and intensity control over the LEDs 10. A practitioner can choose which LED lights are on and their radiance. By illumination of only a few LEDs in the ring of LEDs, this allows for selective sectoral illumination of the retina 101. Illumination can be focused on peripheral versus central retina, allowing a practitioner to focus on one area of the retina. This maintains an advantage over contemporary slit lamp illumination in that larger areas of the retina can be illuminated at one time that afforded by the slit beam. The image 100 also has significantly reduced reflections and enhanced image contrast compared to contemporary designs. This sectoral illumination capability is advantageous for reduction of the embodiment to practice. Patient tolerance to illumination varies significantly, and control of individual LED brightness allows an illumination pattern to be set that is both comfortable for the patient and allows evaluation and treatment of specific areas of the retina. This particular embodiment envisions use of a controller 17 with the LEDs 10 to allow for sectoral illumination. However, the particular embodiment used to control illumination levels and allow sectoral illumination may comprise other methods, including but not limited to a diaphragm, LCD mask, or neutral density filter. There is no capability for this specific control of the illumination pattern in contemporary designs, which limits their practical use in some patients.

Figure 8A:
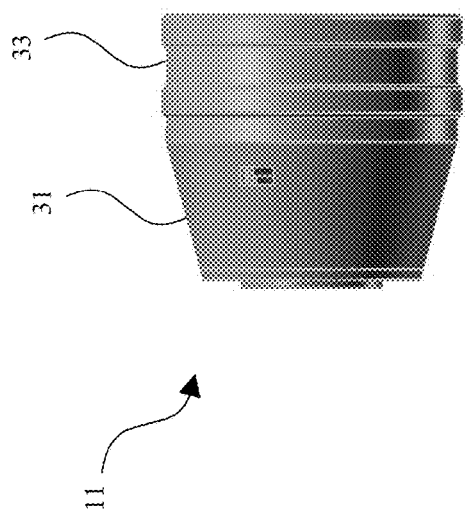
FIGS. 8A-B schematically illustrate a possible configuration of components in an assembled view and exploded view, respectively, that can be used to implement, for example, but not limited thereto, the embodiment shown in FIG. 7, which utilizes a combination of light emitting diodes and a mirrored surface to illuminate the retina.
Figure 8B:
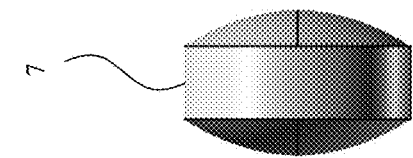
Figure 8B:
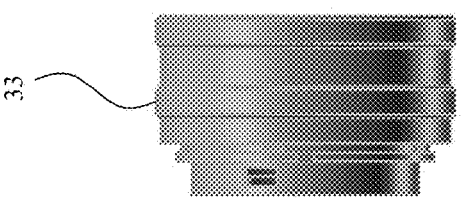
Figure 8B:
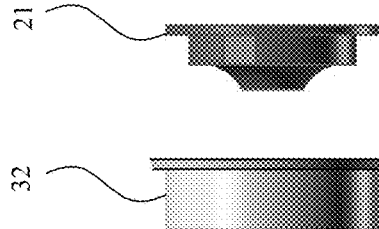
Figure 8B:
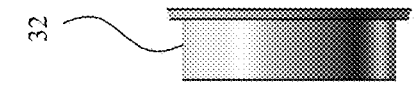
Figure 8B:
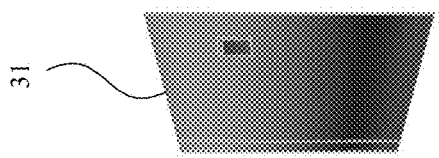
Figure 8B:

In an embodiment, the controller 17 can be triggered by a camera flash to allow all of the LEDS 10 to turn on momentarily at high brightness for the purposes of retinal photography. In an embodiment, the controller 17 can be used to control the intensity of infrared LEDs to allow focusing of the image from the handheld lens and then control interspaced white LEDS, turning them on momentarily at high brightness for the purposes of retinal photography FIGS. 8A-B illustrate a configuration of components in an assembled view and exploded view, respectively, to implement the handheld lens embodiment, for example, but not limited thereto, as described in FIG. 7. A LED mounting 32 surrounds the mirrored surface 21 and the LEDs 10 are mounted on the interior surface of the LED mounting 32. The contact lens 3, LED housing 32, mirrored surface 21, and viewing lens 7 each fit within a LED housing 31 and casing 33. The configuration allows the objective viewing lens 7 and casing 33 of the handheld lens to be separated from the integrated illumination contained in LED housing 31. If a configuration for illumination is needed for a particular application of retinal imaging, one particular LED housing 31 providing one configuration of illumination can be replaced with another LED housing 31 providing another configuration of illumination. The LED housing 31 can also be changed depending on the size of the patient's eye, exemplified by use of the handheld lens on neonatal versus adult patients. The interchangeability eliminates the need for separate lenses for different patient populations.

Figure 9:
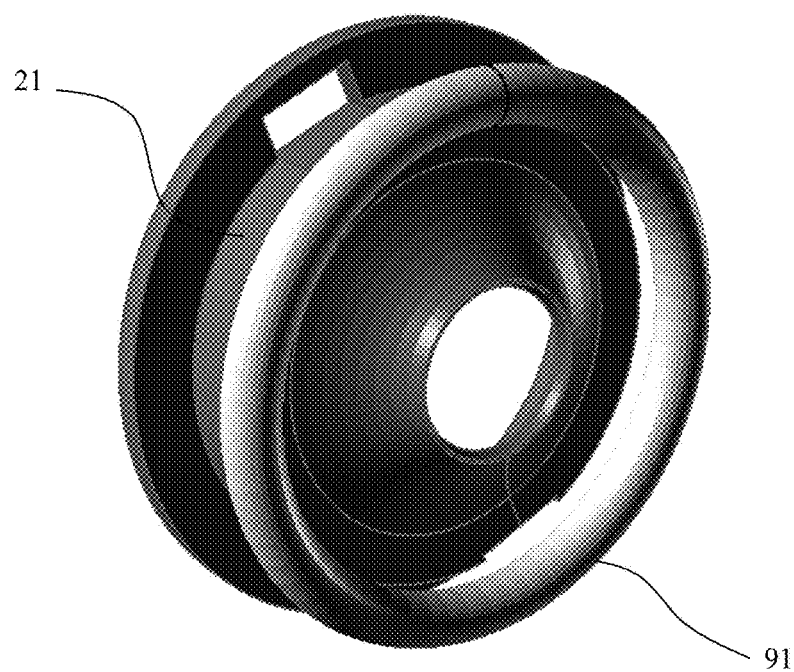
FIG. 9 schematically illustrates one embodiment of the present invention, utilizing a combination of xenon flash lighting and a mirrored surface to illuminate the retina.

FIG. 9 illustrates an embodiment providing for the use of xenon flash lighting 91 in place of LEDs 10. The xenon flash lighting 91 emits light which is reflected off of the mirrored surface 21 and transmitted to the patient's eye. Use of xenon flash lighting 91 provides for a higher intensity light than achieved by LED or fiber optic illumination and eliminates the need to fiber optically couple flash illumination to the handheld lens. In an embodiment xenon flash lighting 91 would be used for retinal photography.

Figure 10:
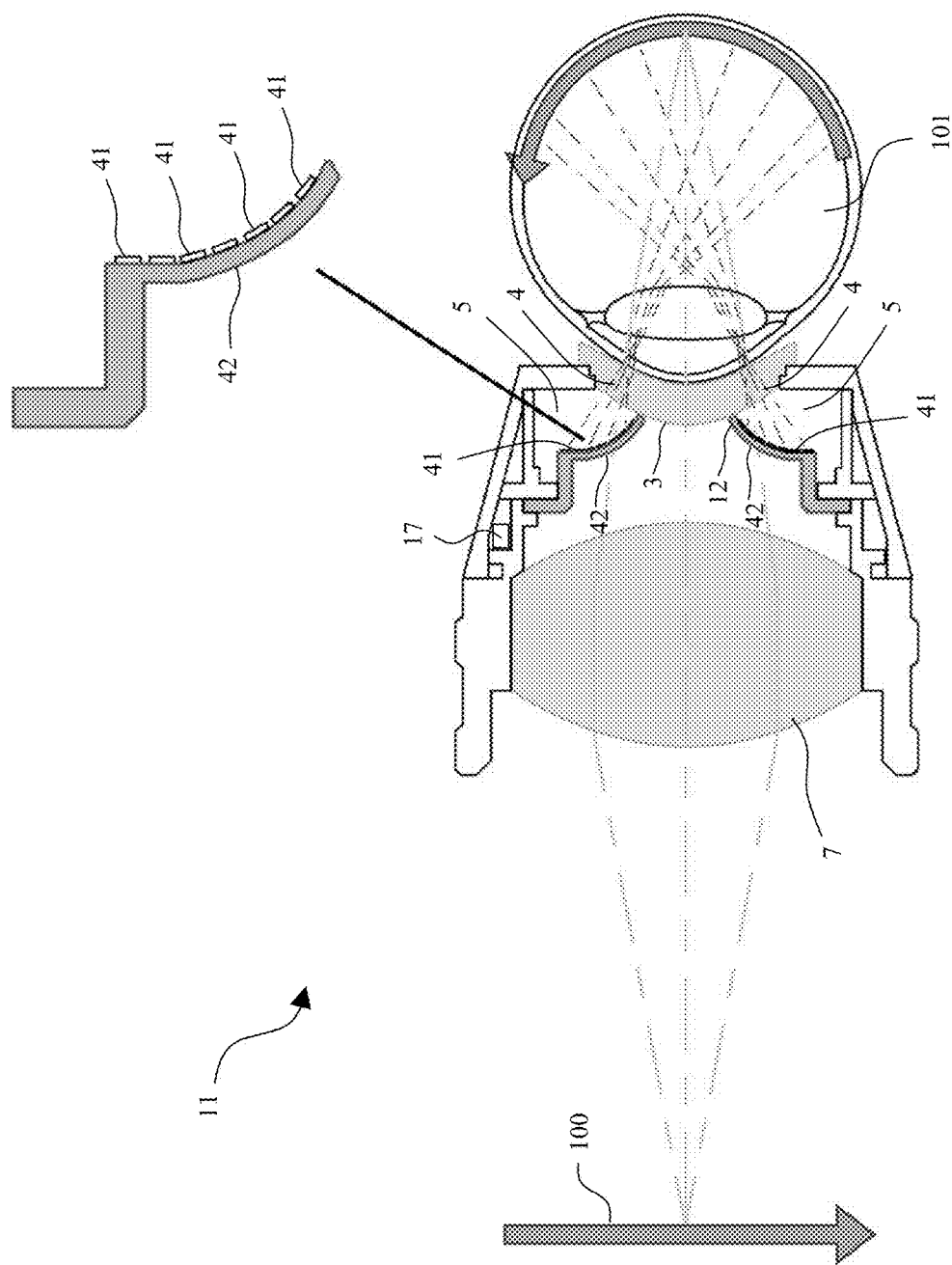
FIG. 10 schematically illustrates one embodiment of the present invention, utilizing light emitting diodes mounted on a curved surface to illuminate the retina.

An embodiment of the present invention, illustrated in FIG. 10, provides for a handheld lens 11 utilizing surface-mounted LEDs 41 on a curved surface 42 to illuminate a patient's retina 101. The surface-mounted LEDs 41 may be high-intensity white, infrared, or colored. Surface-mounted LEDs 41 may be positioned on curved surface 42 so as to provide even illumination across the patient's retina. Light from the surface-mounted LEDs 41 enters the light cavity 5 and is transmitted to the patient's eye through the light channel 4 and contact lens 3. It is through the light channel 4 that light from the surface-mounted LEDs 41 is transmitted to the retina 101. The light channel 4 may be a thinning of the contact lens 3, a portion of the contact lens 3 that differs in power, a gap ground into or provided in the contact lens 3, a gap around or adjacent the contact lens 3, or a space behind or adjacent to the contact lens 3. The light is multidirectional in nature due to the shape of the curved surface 42. The curved surface 42 can be shaped to provide any pattern of illumination needed for a particular application of the handheld lens. The curved surface 42 also serves to prevent the light from entering the central aperture 12 of the lens cavity 15 and the viewing area of the viewing lens 7. Light from the surface-mounted LEDs 41, transmitted through the light channel 4 to the retina 101, reflects back through the contact lens 3 and viewing lens 7 resulting in the image 100.

The embodiment of FIG. 10 provides a matrix of the surface-mounted LEDs 41 to allow an exquisite degree of temporal and spatial control of retinal illumination not available in contemporary designs. This embodiment may be may be advantageous in using the invention in some patient populations depending on application or patient constraints. In particular, placement of the surface-mounted LEDs 41 directly on the curved surface 42 allows for a smaller LED housing 31 than in other embodiments, which may be needed for certain patient populations such as neonates, or for particular applications such a vitreoretinal surgery.

The surface-mounted LEDs 41 can be individually controlled as described for the embodiment of FIG. 8 to allow any pattern of central or peripheral retinal illumination to be provided for the particular application. An embodiment of the present invention allows a practitioner control over the illumination pattern by direct control of individual surface-mounted LEDs 41. A controller 17 is connected to each individual LED or a series of LEDs to allow a practitioner spatial, temporal, and intensity control over the surface-mounted LEDs 41. A practitioner can choose which LED lights are on and their radiance. By illumination of only a few LEDs in the ring of LEDs, this allows for selective sectoral illumination of the retina. Illumination can be focused on peripheral versus central retina, allowing a practitioner to focus on one area of the retina 101. This maintains an advantage over contemporary slit lamp illumination in that larger areas of the retina can be illuminated at one time that afforded by the slit beam. The image 100 also has significantly reduced reflections and enhanced image contrast compared to contemporary designs. This sectoral illumination capability is advantageous to practical use of the invention. Patient tolerance to illumination varies significantly, and control of individual LED brightness allows an illumination pattern to be set that is both comfortable for the patient and allows evaluation and treatment of specific areas of the retina. This particular embodiment envisions use of a controller 17 with surface-mounted LEDs 41 to allow for sectoral illumination. However, the particular embodiment used to control illumination levels and allow sectoral illumination may comprise other methods, including but not limited to a diaphragm, LCD mask, or neutral density filter. There is no capability for this specific control of the illumination pattern in contemporary designs, which limits their practical use in some patients.

In an embodiment, the controller 17 can be triggered by a camera flash to allow all the surface-mounted LEDs 41 to turn on momentarily at high brightness for the purposes of retinal photography. In another particular embodiment, the controller 17 can be used to control the intensity of infrared LEDs to allow focusing of the image from the handheld lens and then control interspaced white LEDS, turning them on momentarily at high brightness for the purposes of retinal photography.

Figure 11B:
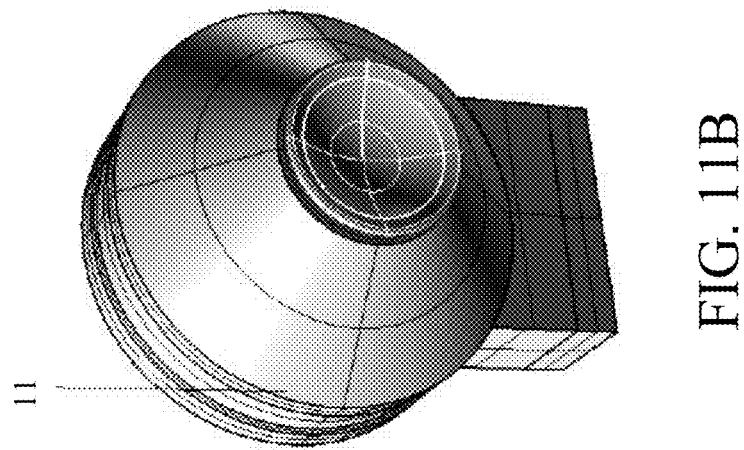
FIGS. 11A-11B schematically illustrate the external casing of an embodiment of the present invention in side ways position and upward position, respectively.
Figure 11A:
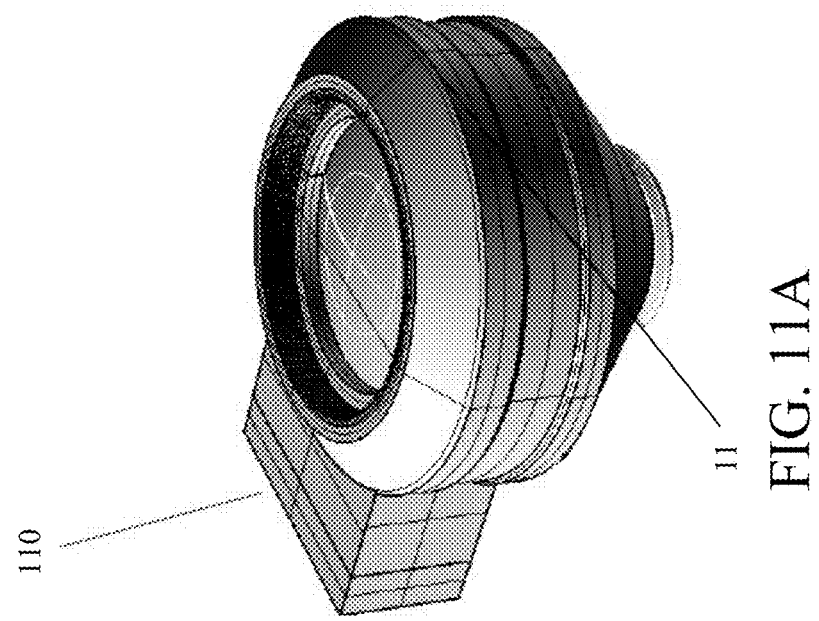

FIGS. 11A-11B shows the outer casing of handheld lens 11 in an exemplary embodiment of the present invention in side ways position and upward position, respectively. A battery compartment 110 is located on the side of the handheld lens 11 to house batteries to power the illumination source, as well as to house the fiber optic cable 2 and light source 1, as required by some embodiments described above. The dimensions of the various embodiment of this invention may be less than, for example, approximately 20% of the size of commercial embodiments of contemporary designs. With a battery powering the self-contained illumination of various embodiments, no external AC power source or external electrical or fiber optic cords are necessary to connect to the handheld lens. The focal point of the handheld lens remains at the standard distance to allow for ophthalmic slit lamp biomicroscopy by a trained practitioner with this lens. While it may be advantageous to have the power source and/or light source provided integrally connected with the hand held lens 11 or completely inside the hand held lens 11, it should be appreciated that it may be provided from an exterior source, or any combination thereof.

While an intended use for this lens is directed towards clinical slit lamp biomicroscopy, the scope of its use and the claims with the current invention include additional applications. In one embodiment the lens will be used for application of laser photocoagulation to the retina in patients requiring this treatment such as diabetics and those with retinal defects. In an embodiment the laser aiming beam and laser application could be provided as conventionally occurs via the slit lamp biomicroscope. However, rather than using the slit illumination of the slit lamp to illuminate the retinal details, built in illumination in the handheld contact lens would serve this function. This has the potential to allow a 165 degree full illumination of the retina during laser application, which is not possible with contemporary designs. It also allows for sectoral retinal illumination with significantly reduced image aberrations than available with contemporary designs.

Figure 12A:
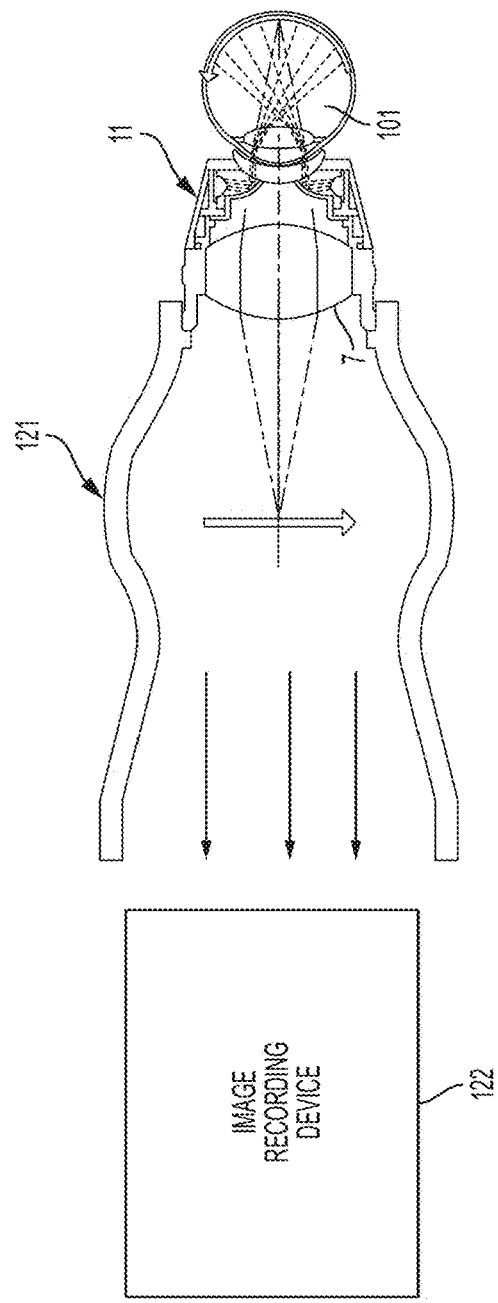
FIGS. 12A-B illustrates a schematic view and a photographic depiction, respectively, of the use of an embodiment of the present invention as part of a system for retinal photography.
Figure 12B:
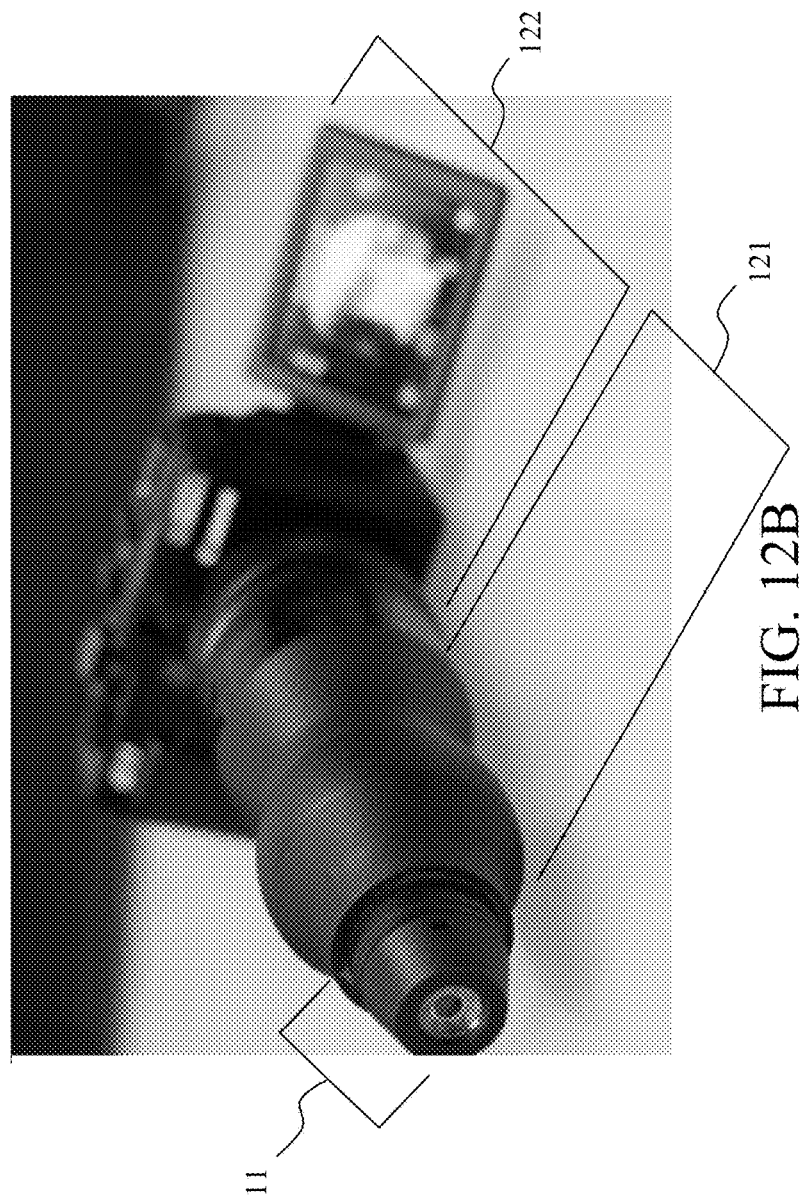

In an embodiment this lens may be adapted for use with existing retinal cameras or other image recording devices as desired or required. FIG. 12A illustrates one such embodiment. The handheld lens 11, designed to provide even illumination of a patient's retina 101 through providing annular illumination, is attached to a lens-to-camera interface 121. The lens-to-camera interface 121 is also attached to an image recording device 122. The lens-to-camera interface 121 comprises the optics and housing needed to couple the image produced by the handheld lens to the image recording device 122 to allow the handheld lens image to be recorded. Most conventional retinal cameras are capable of approximately 60 degrees field of view of the retina, which encompasses only the most central aspects of the retina. Widefield photography requires use of a contact lens, but is not possible with a standard retina camera due to the design of the retina camera illumination. One particular implementation of the embodiment illustrated in FIG. 12A is shown in FIG. 12B.

It should be appreciated that an aspect of the various embodiments of the invention provided throughout this disclosure may include images or data obtained by handheld lens 11 that may be stored or communicated with the image recording device 122 as shown, or other devices not shown. For instance, images (or other data) may be communicated through a transmission module (not shown) to either a local and/or remote location(s). It should be appreciated that the local and/or remote location(s) may include, but are not limited thereto, a user, a processor, a display, a database, an archive, PDA, computer, lap top, network, or any combination thereof. This may enable specialists (or other practitioners or users) to complete diagnostics using the images (or other data) at local or remote locations and enable telemedicine practices (e.g., internet practices, etc.) to be used. In using telemedicine practices (e.g., internet practices, etc.), the images or other data may be transmitted through the transmission module (hardwire, wireless, etc. as desired or required) to a remote location(s) where they are later reviewed by ophthalmologists or other trained specialists. If the image shows that the patient has a disease or defect, the patient may then be referred to a specialist for more testing and treatment. In this situation, images of the hand held lens system/device can be recorded at a primary care clinic without the need for specialists at the primary care clinic to perform the diagnosis. Reviewing images by specialists at a remote location may allow for more efficient processing and diagnostics of the recorded images or other data. This may allow a greater number of patients (or subjects) to be screened for retinal diseases, etc. at a lower overall cost.

In an embodiment it is provided that xenon or LED illumination will be used built into the handheld lens 11. The retina camera can then be adapted to disable its illumination and rely on the self-contained handheld lens illumination to enable widefield retinal photography.

Figure 13A:
FIG. 13A shows a view of a model eye using, for example, the embodiment of FIG. 10.

FIG. 13A shows a view of a model eye using the embodiment of FIG. 10. In the image, only part of the retina 101 is illuminated. The controller 17 is being used to selectively illuminate only this portion of the retina 101.

Figure 13B:
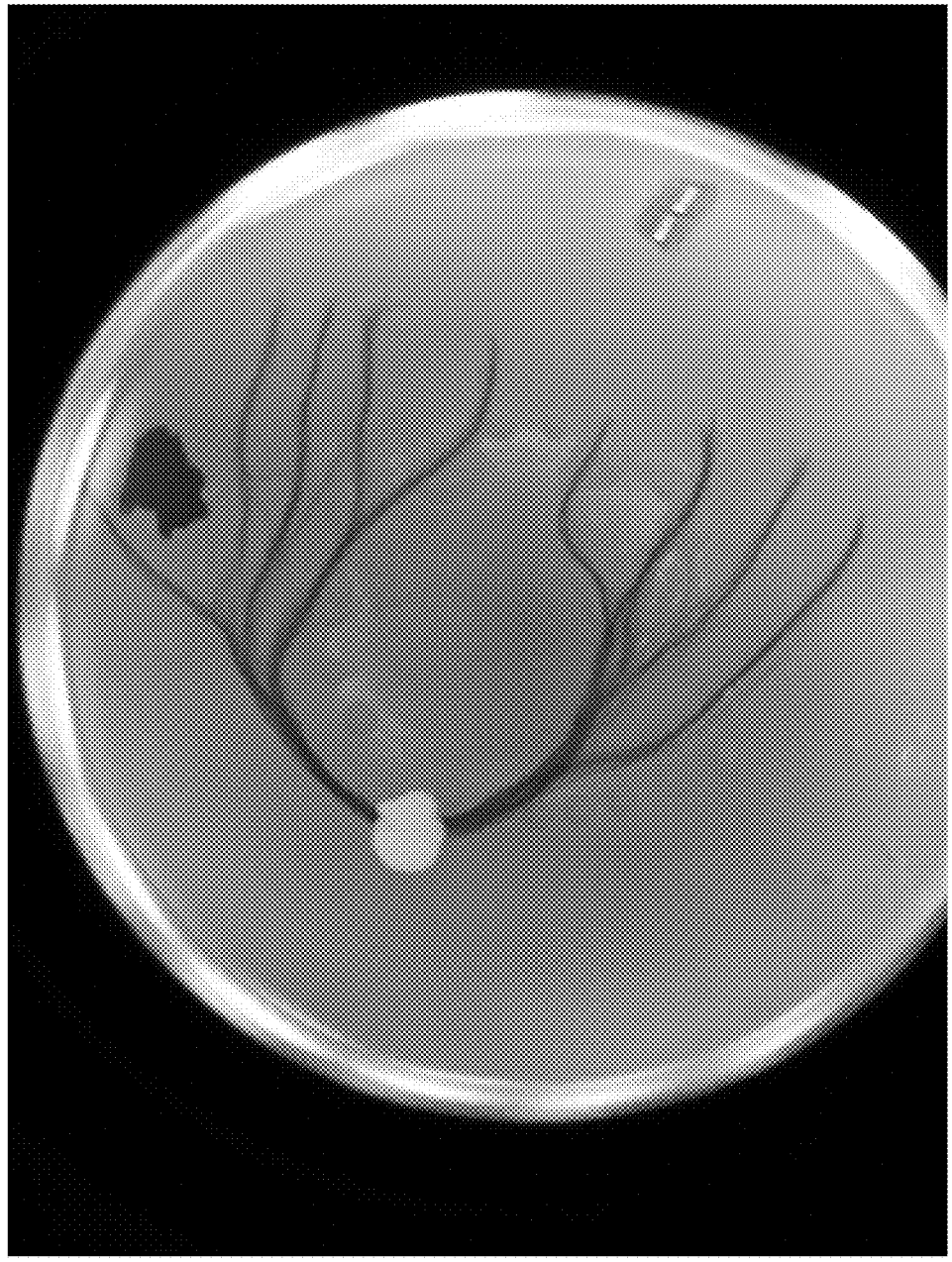
FIG. 13B shows a view of a model eye using, for example, the embodiment of FIG. 10.

FIG. 13B shows a view of a model eye using the embodiment of FIG. 10. Each of surface-mounted LEDs 41 is illuminated, illuminating the patient's retina 101.

Figure 13C:
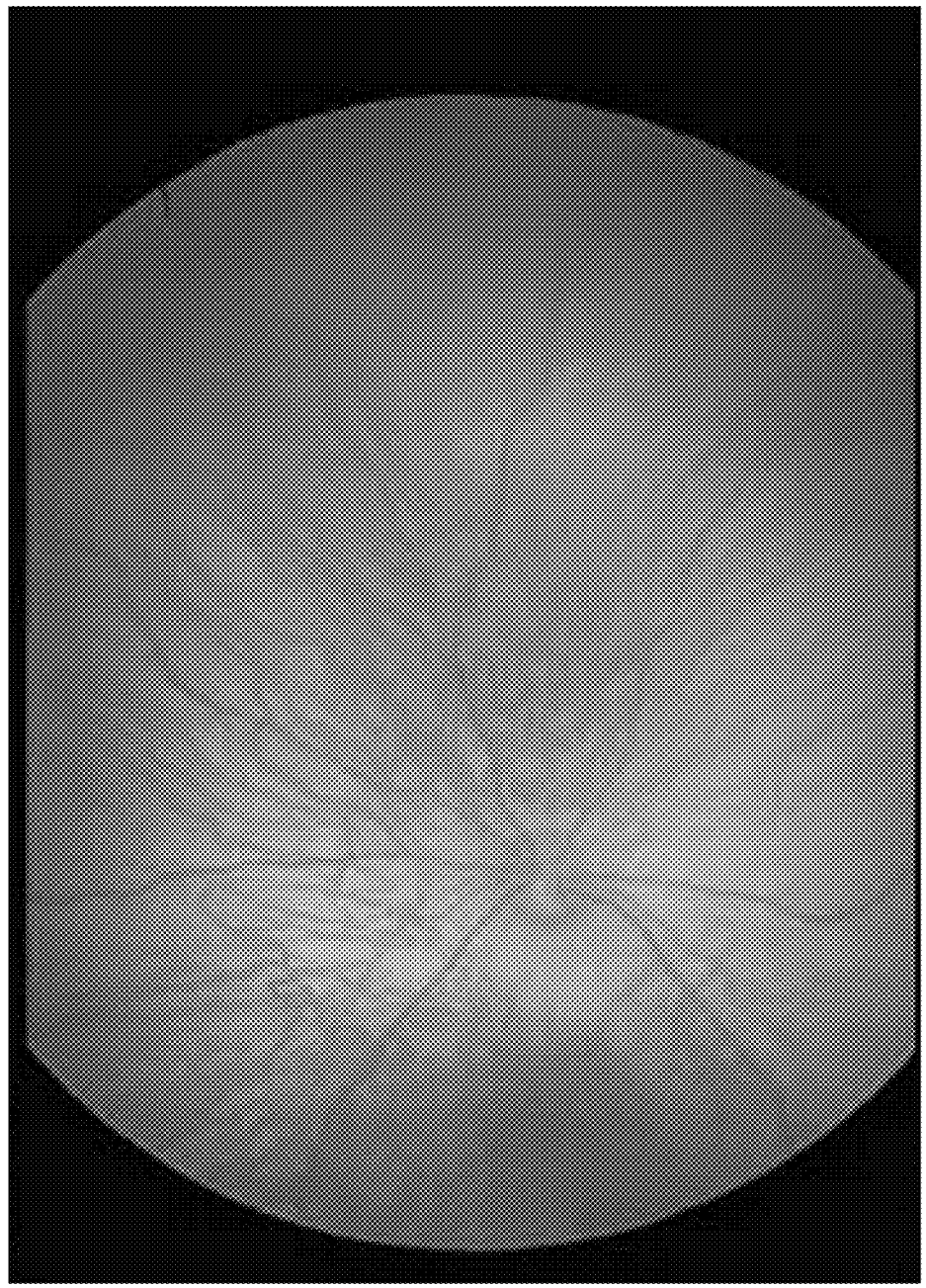
FIG. 13C shows an image taken by a contemporary retinal camera. The image is obscured by corneal haze.

FIG. 13C shows an image taken by a contemporary retinal camera. The image is obscured by corneal haze. Comparing FIGS. 13B and 13C reveals that the handheld lens of FIG. 10 is able to achieve a similar or higher quality image than contemporary retinal cameras.

In another embodiment this self-illuminated handheld lens 11 may be used to adapt existing surgical vitreoretinal contact lenses used for vitreoretinal surgery. Handheld lens 11 will provide illumination of the retinal surface to enable better visualization during vitreoretinal surgery. It would also potentially permit bimanual vitreoretinal surgery as a separate handheld light fiber to illuminate the retina as used in conventional vitreoretinal surgery may no longer be necessary if the surgical vitreoretinal contact lens provides sufficient illumination. In one particular embodiment, individual control over the pattern of retinal illumination would be provided using the controller 17 or other method, for example, as described for the embodiments of FIG. 7, FIG. 8, and FIG. 10.

Figure 14:
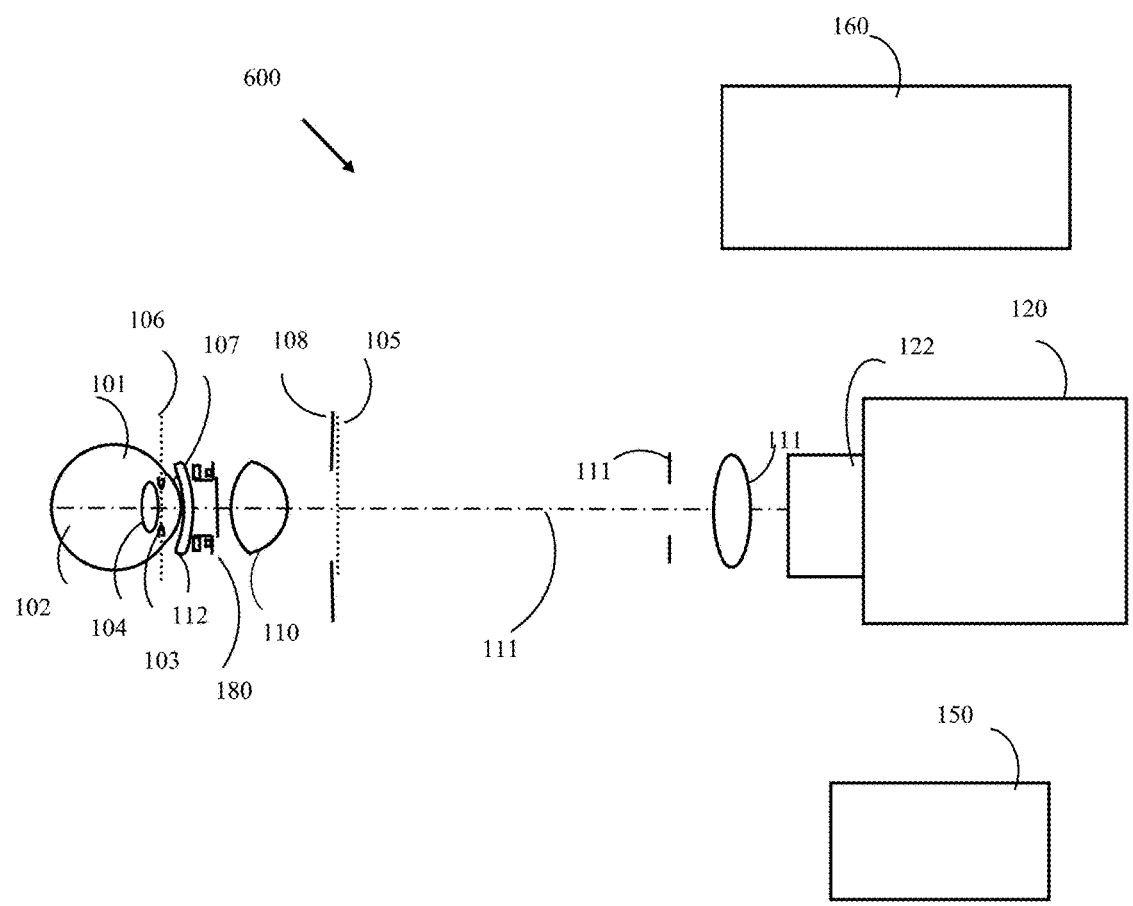
FIG. 14 shows schematically a wide field fundus camera implemented having a front LED illumination module.

Referring to FIG. 14, the objective lens 110 may preferably be a wide field aspherical lens and is located near a first end of the fundus camera 600. The objective lens 110 defines a symmetric viewing axis 111 and a working plane 106 of the fundus camera 600. When a subject eye 101 is aligned with the fundus camera 600 for fundus viewing, a subject pupil 103 is about to position at the working plane 6 and the LED illumination module 180 are projected into subject pupil 3 to illuminate the subject retina 102 for alignment and for photographing. At a proper alignment, the objective lens 110 produces a first retina image near its back focal plane 105, and the first retina image is then re-imaged into the digital camera 120. The illumination aperture 8 is located at the back focal plane 105 so as to define illumination area on the subject retina 102. Also illustrated is subject crystalline lens 104.

At a proper alignment, objective lens 110 also forms an image of the subject pupil 103 onto the plane of optical stop 114, which thus defines a small, virtual viewing window on the subject pupil 103 for the camera 120 to look through into the retina 102.

In an embodiment, the wide field fundus camera 600 may require a static field of view of 120 degrees or wider on the subject retina 102. In an embodiment, the objective lens 110 has an optical power of about 120 D and a diameter of about 18 mm. The objective lens 110 has thus a back focal length of shorter than 8 mm and a small working distance of approximate 4 millimeters with respect to the subject cornea 107.

In an embodiment, a contact lens 112 is preferably positioned in front of the aspherical objective lens 110 and in direct contact with the subject cornea 107. The contact lens 112 may or may not have optical power. For example, in an embodiment, a contact lens 112 is incorporated with the aspherical objective lens 110 to produce a first retinal image of the retina 102. In an embodiment, the contact lens may have a diameter of about 110 mm to fit for small eye ball 101 of the infants.

Figure 15:
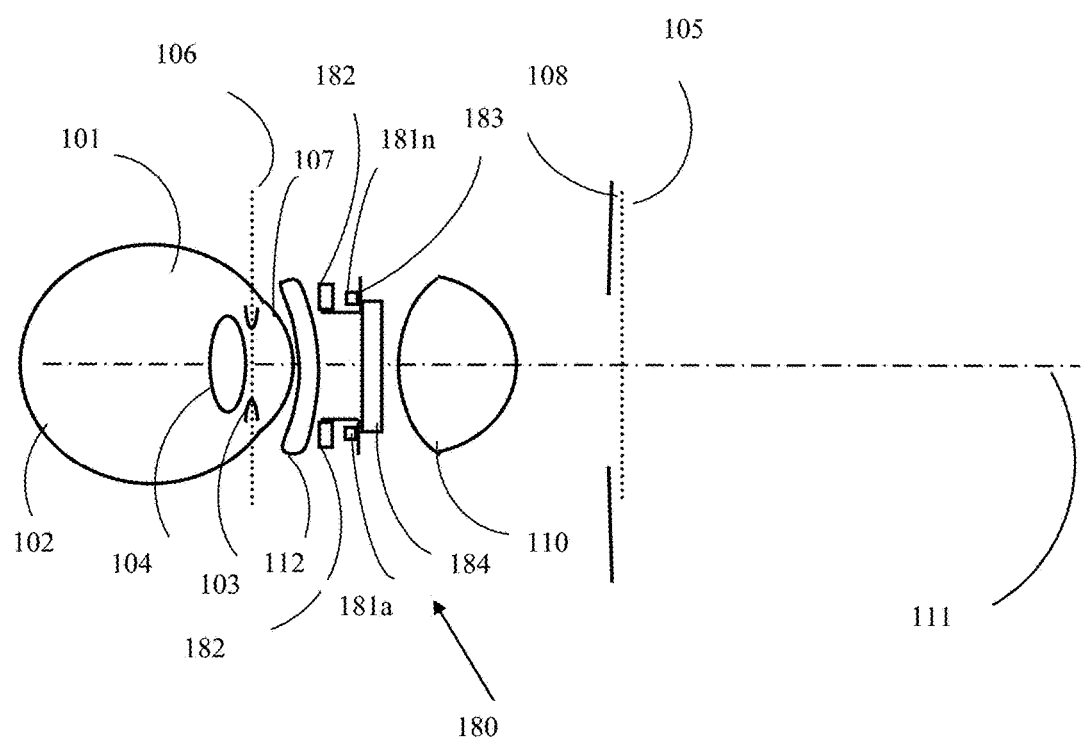
FIG. 15 shows schematically an embodiment of the front LED illumination module, and furthermore with cross polarization.

FIG. 15 shows schematically an embodiment of the front LED illumination module 180 as shown in FIG. 14, and furthermore with an optional cross polarization. The front LED illumination module 180 includes a plurality of LEDs 181a-181n, a first polarizer 182, a light baffle 183, and a second polarizer 184. The plurality of LEDs 181a-181n may be high brightness, surface mounted, white LEDs. The LEDs are mounted in a circle around the symmetric viewing axis 111 of the objective lens 110. The first polarizer 182 is shaped and attached to cover the plurality of LEDs 181a-181n, and the second polarizer positioned 184 is positioned in the viewing path of said digital camera 120. The light baffle 183 is made of black to block direct view of the LEDs 181a-181n from the digital camera 120. The light baffle 183 may be made of metal so that it can also serve as a heat sink to the LEDs 181a-181n.

In an embodiment, the LEDs 181a-181n are positioned in a circle of approximate 7 mm in diameter. The light baffle 183 defines a viewing channel of the objective lens 110 with an aperture of approximate 5.5 mm.

Figure 16:
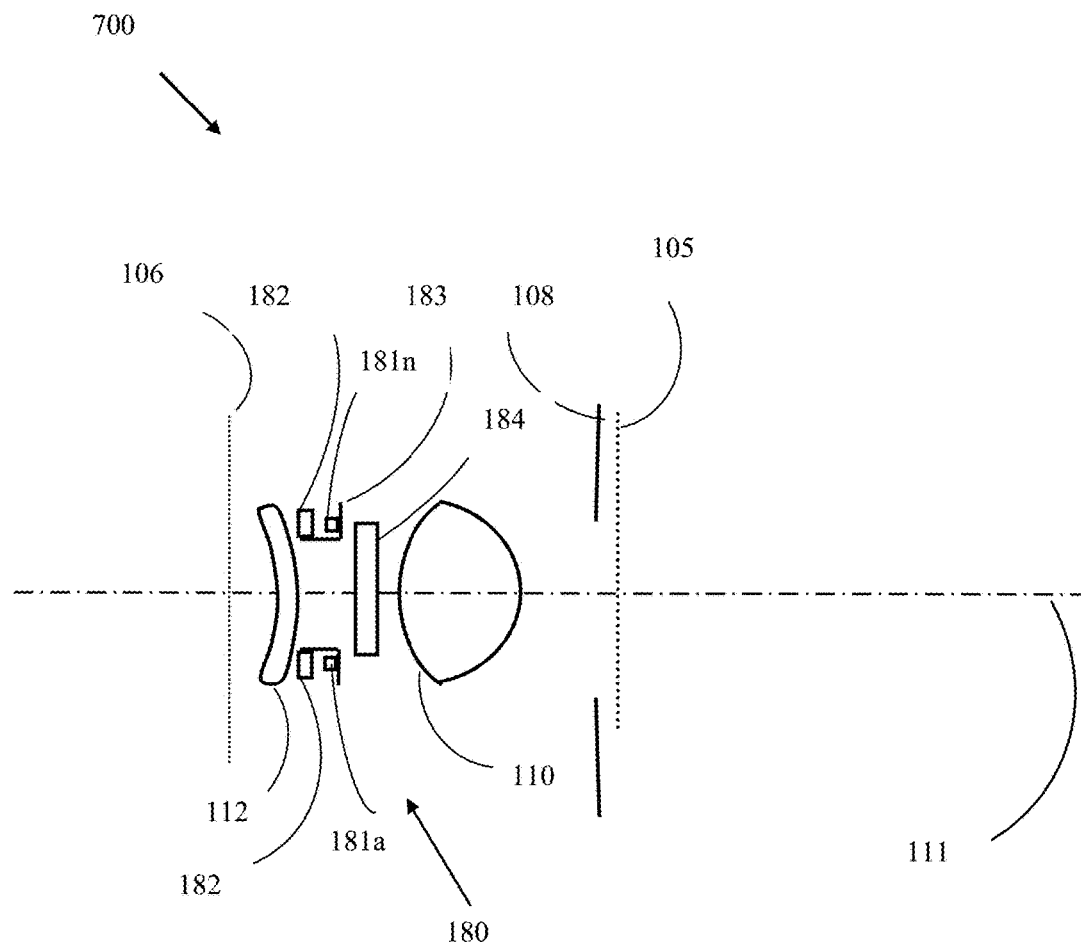
FIG. 16 shows schematically a self-illuminated wide angle contact lens implemented a front LED illumination module with cross polarization.

FIG. 16 shows schematically a self-illuminated wide angle contact lens 700 implemented having a front LED illumination module 180 with cross polarization. The self-illuminated wide angle contact lens 700 consists of primarily a contact lens 112, a front LED illumination module 180, and an objective lens 110. The front LED illumination module 180 includes a plurality of LEDs 181a-181n, a first polarizer 182, a light baffle 183, and a second polarizer 184.

FIG. 17 shows a CAD drawing of self-illuminated wide angle contact lens 800 implemented a front LED illumination module 180 with cross polarization. The front LED illumination module 180 includes a plurality of LEDs 181a-181n, a first polarizer 182, a light baffle 183, and a second polarizer 184.

FIG. 18 shows a front view of FIG. 17 of a LED circular array 181 for front LED illumination. In the embodiment, four LEDs form the plurality of LEDs 181a-81n.

FIG. 19 shows a side view of FIG. 17 of a LED circular array 181 for front LED illumination.

Figure 20:
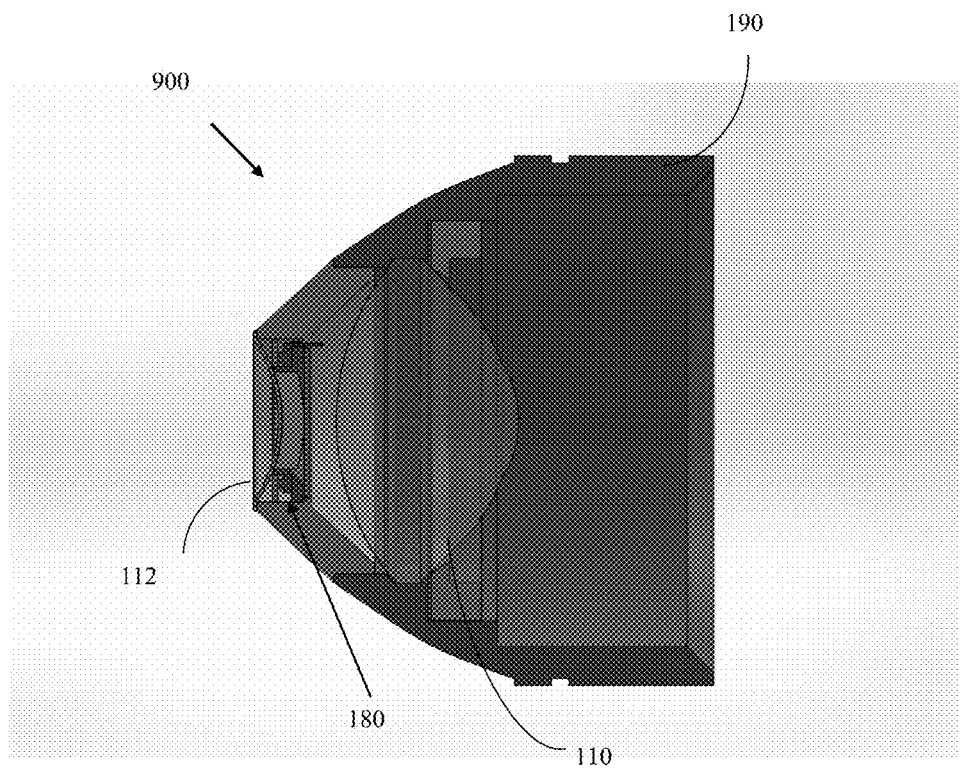
FIG. 20 shows a cross section drawing of a self-illuminated handheld lens implemented having a front LED illumination module with cross polarization.

FIG. 20 shows a cross section drawing of a self-illuminated handheld lens 900 implemented having a front LED illumination module 180 with cross polarization. The self-illuminated handheld lens 900 consists of primarily a contact lens 112, a front LED illumination module 180, an objective lens 110 and a lens housing 190.

Figures 21, 22:
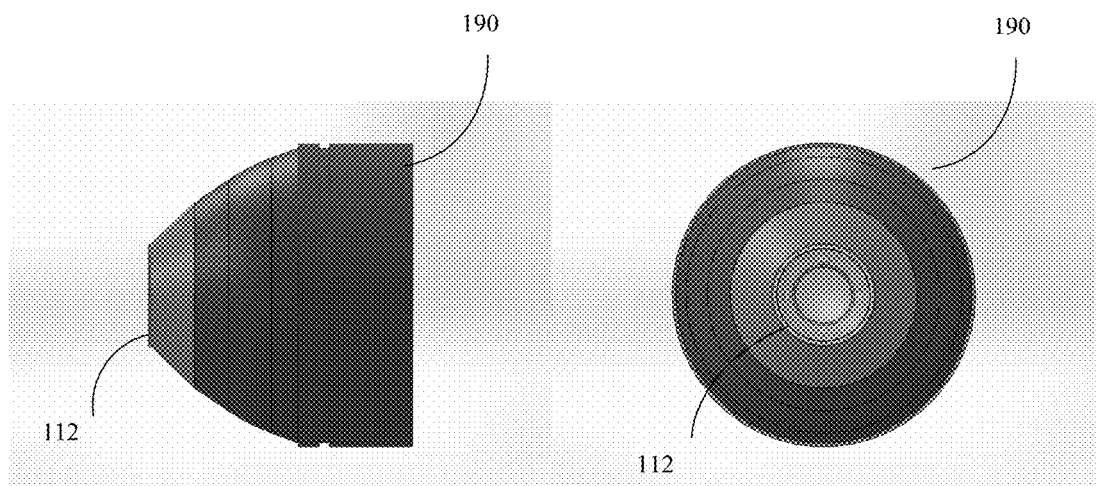
FIG. 21 shows a side view of the self-illuminated handheld lens of FIG. 20.
FIG. 22 shows a front view of the self-illuminated handheld lens of FIG. 20.

FIG. 21 shows a side view of FIG. 20 of the self-illuminated handheld lens 900.

FIG. 22 shows a front view of FIG. 20 of the self-illuminated handheld lens 900.

In short, an aspect of the present invention provides a handheld fundus lens with built in self-illumination to permit widefield viewing of the retina. Current handheld fundus lenses rely on external slit lamp biomicroscope illumination of the retina, which has the disadvantage of significant image aberrations and reflections as well as a limited slit area of retina that can be viewed at one time. The novel illumination design of the various embodiment of the present invention overcomes all of these limitations to allow more detailed examination of the entire retinal surface in any pattern needed and permit safer surgical procedures to be performed on the retina.

Accordingly, the revolutionary medical device (and related method) of the various embodiments will allow retina specialists their first clear detailed view of the retina during clinical exam at the slit lamp in 100 years. Further, it has the potential to completely change the way ophthalmologists examine the retina, and to dramatically improve the standard to which we are held on the detail of our clinical retina exam. It provides the potential to bring the same technological capabilities that we currently have in retina photography to our day to day clinical examination of the eye. In some cases it may eliminate the need for separate procedures to obtain retina photography as the photographic view at the ophthalmic slit lamp may be of sufficient. This device (and related method) can also potentially transform how both laser surgical procedures and vitreoretinal surgery is practiced. It will be immediately clear exactly were the laser aiming beam is located on the surface of the retina in a way which is not currently possible. During vitreoretinal surgery it may allow use of bimanual procedures, instead of rendering one hand relegated to holding the illumination probe. This device will substantially improve patient care by increasing the quality of the exam, allowing better diagnosis of retinal disease. It will also render laser and surgical procedures on the retina much safer by providing a clear panoramic view of the retina. This is, simply put, one of those few devices that has the possibility to transform how we practice ophthalmology.

Commercial potential for this device (and related methods) is extremely high. There is no competing technology currently in the marketplace other than non-illuminated handheld fundus lenses with their associated disadvantages. The commercial potential will be impacted by price point over these existing lenses. It is therefore expected that ophthalmology clinics in the United States and various countries around the world will purchase these lenses if they are made available.

It should be appreciated that various sizes, dimensions, contours, rigidity, shapes, flexibility and materials of any of the embodiments discussed throughout may be varied and utilized as desired or required.

It should be appreciated that as discussed herein, a subject may be a human or any animal. It should be appreciated that an animal may be a variety of any applicable type, including, but not limited thereto, mammal, veterinarian animal, livestock animal or pet type animal, etc. As an example, the animal may be a laboratory animal specifically selected to have certain characteristics similar to human (e.g. rat, dog, pig, monkey), etc. It should be appreciated that the subject may be any applicable human patient, for example.

The devices, systems, compositions, computer program products, and methods of various embodiments of the invention disclosed herein may utilize aspects disclosed in the following references, applications, publications and patents and which are hereby incorporated by reference herein in their entirety:

1. U.S. Pat. No. 3,944,341, Mar. 16, 1976, to Oleg Pomerantzeff, "Wide-Angle Ophthalmoscope and Fundus Camera."

2. U.S. Pat. No. 5,822,036, Oct. 13, 1998, to Norbert Massie, "Eye Imaging Unit Having a Circular Light Guide."

3. U.S. Pat. No. 7,048,379, May 23, 2006, to Joseph Miller and James Schwiegerling, "Imaging Lens and Illumination System."

4. International Patent Application Publication No. WO 2004/082465 A2, Miller, et al., "An Imaging Lens and Illumination System", Sep. 30, 2004.

In summary, while the present invention has been described with respect to specific embodiments, many modifications, variations, alterations, substitutions, and equivalents will be apparent to those skilled in the art. The present invention is not to be limited in scope by the specific embodiment described herein. Indeed, various modifications of the present invention, in addition to those described herein, will be apparent to those of skill in the art from the foregoing description and accompanying drawings. Accordingly, the invention is to be considered as limited only by the spirit and scope of the following claims, including all modifications and equivalents.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Unless clearly specified to the contrary, there is no requirement for any particular described or illustrated activity or element, any particular sequence or such activities, any particular size, speed, material, dimension or frequency, or any particularly interrelationship of such elements. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all sub ranges therein. Any information in any material (e.g., a United States/foreign patent, United States/foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

What is claimed is:

1. A self-illuminated handheld lens for wide angle retinal viewing of a subject eye, comprising:
    an aspherical objective lens having a symmetric viewing axis and defining a viewing channel;
    plurality of LEDs positioned around said viewing axis and configured to emit light to illuminate said subject eye;
    an electronic controller powering said plurality of LEDs and controlling each individual LED or a series of LEDs independently;
    a light baffle configured to block stray light of said plurality of LEDs from getting into said viewing channel; and
    cross polarization means incorporated between said plurality of LEDs and said viewing channel of said aspherical objective lens, wherein said cross polarization means comprises a first polarizer to polarize said light emitted from said plurality of LEDs and a second polarizer positioned in said viewing channel of said aspherical objective lens.

2. The self-illuminated handheld lens of claim 1, further comprising:
    a contact lens positioned in front of said aspherical objective lens to be applied to said subject eye.

3. The self-illuminated handheld lens of claim 2, wherein said contact lens has a diameter approximate 10 mm.

4. The self-illuminated handheld lens of claim 1, wherein said aspherical objective lens has a field of view of 120 degrees or wider on said retina.

5. The self-illuminated handheld lens of claim 1, wherein said plurality of LEDs are each a high brightness, surface mounted, white light LED.

6. The self-illuminated handheld lens of claim 1, wherein said light baffle is made of black outside said viewing channel.

* * * * *